(12) United States Patent
Dorairaj et al.

(10) Patent No.: US 8,298,392 B2
(45) Date of Patent: Oct. 30, 2012

(54) MICROFLUIDIC DEVICES AND METHODS OF USING SAME

(75) Inventors: Rathissh Dorairaj, Louisville, KY (US); Robert S. Keynton, Louisville, KY (US); Thomas J. Roussel, Jr., Louisville, KY (US); Carolyn M. Klinge, Louisville, KY (US); Wasana Sumanasekera, Louisville, KY (US); Gamini Sumanasekera, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 12/988,713

(22) PCT Filed: Apr. 21, 2009

(86) PCT No.: PCT/US2009/041279
§ 371 (c)(1),
(2), (4) Date: Dec. 3, 2010

(87) PCT Pub. No.: WO2010/042247
PCT Pub. Date: Apr. 15, 2010

(65) Prior Publication Data
US 2011/0100817 A1    May 5, 2011

Related U.S. Application Data

(60) Provisional application No. 61/046,664, filed on Apr. 21, 2008, provisional application No. 61/050,411, filed on May 5, 2008.

(51) Int. Cl.
*G01N 27/447*    (2006.01)
*G01N 27/453*    (2006.01)

(52) U.S. Cl. .......... 204/451; 204/601; 977/742
(58) Field of Classification Search .......... 204/450–455, 204/600–605; 977/788, 932, 742, 601, 452
See application file for complete search history.

(56) References Cited

U.S. PATENT DOCUMENTS

| | | |
|---|---|---|
| 6,685,810 B2 | 2/2004 | Noca et al. |
| 6,773,567 B1 | 8/2004 | Wolk |
| 6,919,046 B2 | 7/2005 | O'Connor et al. |
| 7,290,667 B1 | 11/2007 | Bakajin et al. |
| 2004/0248167 A1 | 12/2004 | Quake et al. |
| 2005/0079519 A1 | 4/2005 | Boles et al. |
| 2005/0106605 A1 | 5/2005 | Amshey et al. |
| 2006/0051858 A1 | 3/2006 | Combette et al. |

OTHER PUBLICATIONS

Ahern et al., "Characterization of Polyacrylamide Gel Formation and Structure by Surface-Enhanced Raman Spectroscopy," Langmuir, 1988, vol. 4, pp. 1162-1168.

Bakafin et al., "Carbon Nanotube Based Microfluidic Elements for Filtration and Concentration," International Conference on Miniaturized Chemical and Biochemical Analysts Systems, Oct. 5-9, 2003, Squaw Valley, California, USA.

Baselga et al., "Network Defects in Polyacrylamide Gels," Eur. Polym. J., 1989, vol. 25(5), pp. 471-475.

(Continued)

*Primary Examiner* — J. Christopher Ball
(74) *Attorney, Agent, or Firm* — Stites & Harbison PLLC; Terry L. Wright; David W. Nagle, Jr.

(57) ABSTRACT

The presently-disclosed subject matter provides microfluidic devices comprised of two or more carbon nanotube membranes disposed at predetermined intervals within a microchannel. Further provided are methods of using the same for the electrokinetic separation of one or more molecules of interest from a sample.

23 Claims, 18 Drawing Sheets

OTHER PUBLICATIONS

Furlong et al., "A Microfabricated Device for the Study of the Sieving Effect in Protein Electrophoresis," 18th Annual International Conference of the IEEE Engineering in Medicine and Biology Society, Amsterdam, 1996, pp. 248-249.

Hecht et al., "Structural Inhomogeneities in the Range 2.5-2500 A in Polyacrylamide Gels," Macromolecules, 1985, vol. 18, pp. 2167-2173.

Iles et al., "Bonding of Soda-Lime Glass Microchips at Low Temperature," Proceedings of 2006 International Conference on Microtechnology in Medicine and Biology, May 2006, Okinawa, Japan, pp. 109-111.

Jo et al., "Three-Dimensional Micro-Channel Fabrication in Polydimethylsiloxane (PDMS) Elastomer," J. Microelectromechanical Sys., Mar. 2000, vol. 9, No., 1, pp. 76-81.

Kozulic, B, "Prospective: Models of Gel Electrophoresis," Anal. Biochem., 1995, vol. 231: 1-12.

Nakanishi et al., "Condition optimization, reliability evaluation of $SiO_2$-$SiO_2$ HF bonding and its application for UV detection micro flow cell," Sensors and Actuators, 2000, vol. 83, pp. 136-141.

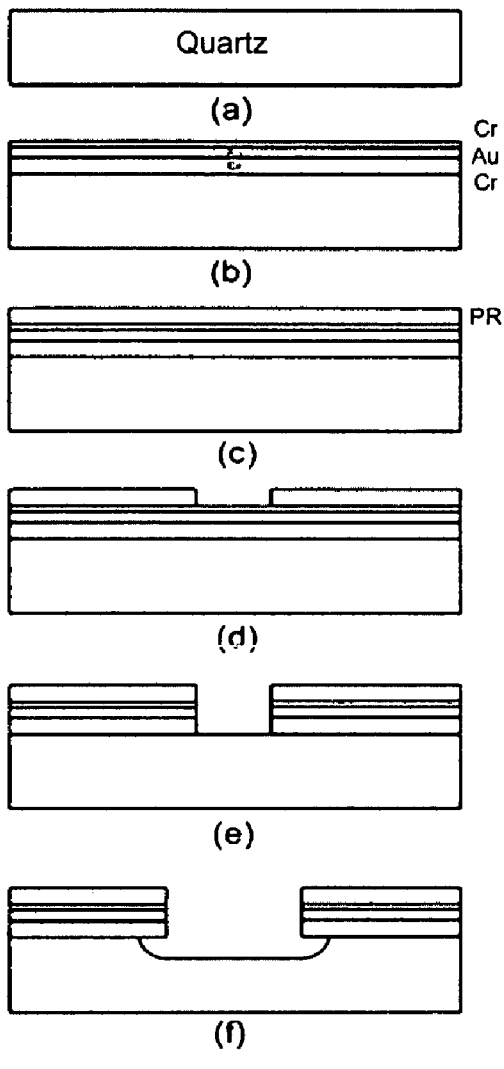
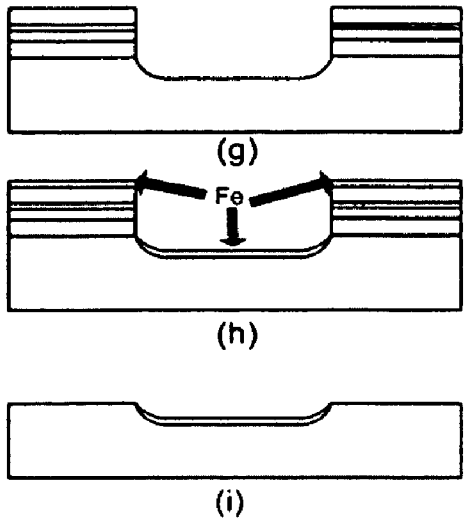
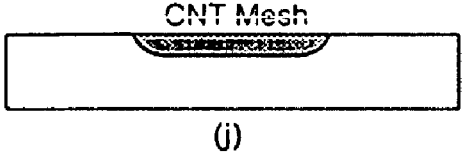
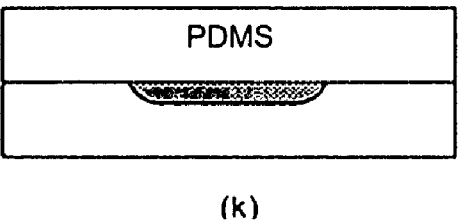
FIGS. 2(a) – 2(k)

MICROFLUIDIC DEVICES AND METHODS OF USING SAME

RELATED APPLICATIONS

This application claims priority from U.S. Provisional Application Ser. No. 61/046,664, filed Apr. 21, 2008, and U.S. Provisional Application Ser. No. 61/050,411, filed May 5, 2008; each of which are incorporated herein by this reference.

GOVERNMENT INTEREST

Subject matter described herein was made with U.S. Government support under Grant Number EEC-0438604 awarded by the National Science Foundation-Partnerships for Innovation. The government has certain rights in the presently-disclosed subject matter.

TECHNICAL FIELD

The presently-disclosed subject matter relates to microfluidic devices and methods of using the same for the separation of one or more molecules from a sample. In particular, the presently-disclosed subject matter relates to microfluidic devices that are comprised of two or more carbon nanotube membranes, and which can be used to electrokinetically separate one or more molecules of interest from a sample.

BACKGROUND

Gel electrophoresis ("GE") is a commonly used electrophoretic separation technique for the analysis of proteins and nucleic acids. GE uses a polymer-based sieving matrix composed of a polyacrylamide gel (e.g., for separation of proteins) or an agarose gel (e.g., for separation of nucleic acids, such as DNA or RNA). Although GE is a mature technique, with several thousands of publications since the 1950s, the field has remained a subject of intense investigation [1]. Indeed, many disadvantages of the current polymer-based sieving matrix approaches for GE have been identified and include lack of repeatability in the production/polymerization of the sieving matrix, single use, and inability to reproduce the same result for similar experiments. Also, the concentration, cross-link density, and rate of formation of the gel can further affect the optical properties, rigidity, and pore size [2]. Other causes of concern with current GE techniques include Joule heating, non-uniform polymerization [4], adhesion of the gel to the support [3] and structural inhomogeneities [5, 6]. Finally, the polymerization of the components used to produce the gels can be significantly affected by slight changes in humidity, temperature, monomer and cross-linker concentration and/or mixture ratio, and personnel performing the process (i.e., technician dependent). As a result, significant variations often exist between experiments performed by the same individual at different times or performed by different individuals in different laboratories. Accordingly, experimental reproducibility is a major problem with current GE techniques and significantly influences the results when repeated experiments are needed to verify a biological research outcome.

Despite the inherent limitations in current GE techniques, however, separation science has continued to play a vital role in chemical and biomedical analyses, and remains indispensable in a wide variety of fields including proteomics, genetics, clinical diagnostics, environmental protection and forensics. The ever increasing need for advancements in proteomics and genetics for combating disease and furthering the understanding of biological systems has thus necessitated the need for superior separation tools. Therefore, researchers have begun to investigate the feasibility of microfabrication for the separation of one or more molecules in a particular sample.

To date, however, only a few investigators have addressed the need to develop alternative GE techniques based on microfabrication methodologies. For example, some researchers, who recognized the limitations of current macroscale polyacrylamide gel electrophoresis (PAGE) techniques, have developed a microfabricated electrophoretic device to study the sieving effect in protein electrophoresis [4]. Such a device included a fluidic channel filled with an "artificial gel," which consisted of a series of staggered posts approximately 2 micrometers in diameter, with the post pitch determining the pore size of the "gel." Proteins were observed to migrate through the sieving matrix in this artificial gel, but no reproducible results were obtained by employing this system, and the system was not able to demonstrate the ability to separate the proteins. Further, the fabrication methodology used to produce this microfabricated electrophoretic device was elaborate, and the lithography procedure that was employed ultimately determined the minimum pore size that could be attained using this approach, thus suggesting that nanoporous membranes, with pore sizes in the order of tens of nm which are needed for some biological separations, could not be produced with conventional microfabrication techniques.

Other researchers have utilized a method of integrating carbon nanotube growth and traditional microfabrication technology to create a "nanotube mesh" inside microchannels [7], which was used for filtering fluorescent beads. The beads, which were about 200 nm in diameter, were released and collected by applying a back pressure to the mesh. However, no electrokinetic separation of molecules could be accomplished by this method. In fabricating the microchannel, the silicon substrate that was used to create the microchannel was bonded to a glass coverslip by anodic bonding, and thus, because of the use of a semiconducting material, electrophoretic separation could not be performed. Also, since fluid flow was pressure driven, separation was completely based on analyte size. Analytes that require charge-based separation simply could not be separated by this technique. Finally, because that microchannel was etched in silicon, a semiconductor, the material rendered the device incompatible with electrochemical detection, which is one of the preferred detection methodologies in micro total analytical systems.

Accordingly, there remains a need in the art for an improved microfluidic device and method of using the same that can effectively be used to separate molecules electrokinetically, including separation by electrophoresis and electroosmosis. In particular, there remains a need in the art for a carbon nanotube-based microfluidic device that is capable of electrokinetically separating multiple biochemical analytes, including proteins and nucleic acids, in a sample of interest.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In some embodiments of the presently-disclosed subject matter, a microfluidic device is provided that comprises: an input reservoir for receiving a sample containing one or more molecules of interest; a microchannel in fluid communication with the input reservoir; two or more carbon nanotube membranes; and a means for generating an electric field through the microchannel such that the electric field induces molecules from the sample in the input reservoir to migrate into the microchannel and up to or through the carbon nanotube membranes to thereby produce electrokinetic separation of the molecules in the sample.

In some embodiments of the presently-disclosed subject matter, a microfluidic device is provided that comprises: an input reservoir for receiving a sample containing one or more molecules of interest; a plurality of microchannels, wherein each microchannel is in fluid communication with the input reservoir; two or more carbon nanotube membranes disposed at predetermined intervals within each microchannel; and a means for generating an electric field through each microchannel such that the electric field induces molecules from the sample in the input reservoir to migrate into each of the microchannels and up to or through the two or more carbon nanotube membranes, thereby producing electrokinetic separation of molecules from the sample. In some embodiments, each of the microchannels is substantially parallel to each other microchannel.

In some embodiments, the carbon nanotube membrane is grown by self-assembly on a surface of the microchannel. In some embodiments, the carbon nanotube membrane is comprised of carbon nanotubes, which, in some embodiments, are about 15 nm to about 135 nm in diameter. In some embodiments, each carbon nanotube membrane includes irregularly sized pores that are defined between the carbon nanotubes and which, in some embodiments, are about 50 nm to about 200 nm in diameter.

With regard to the carbon nanotube membranes of the presently-disclosed microfluidic devices, in some embodiments, each of the carbon nanotube membranes forms a strip that is positioned transverse to the longitudinal axis of the microchannel. In some embodiments, the carbon nanotube membranes, which form the strips, span the width of the microchannel. In some embodiments, each strip is about 40 μm to about 120 μm wide.

In some embodiments, the carbon nanotube membranes are disposed at predetermined intervals within the microchannel, which range from about 50 μm to about 1200 μm. In some embodiments, the predetermined intervals vary between each carbon nanotube membrane. In some embodiments, the predetermined intervals are uniform along the length of the microchannel.

An exemplary microfluidic device of the presently-disclosed subject matter, in some embodiments, includes a pair of electrodes as a means for generating an electric field. In some embodiments, a first electrode is provided that is positioned at a first end of the microchannel near the input reservoir, and a second electrode that is positioned at a second end of the microchannel. In some embodiments, the input reservoir and the microchannel of an exemplary microfluidic device is comprised of either quartz, silicon, alumina, glass, plastic, or combinations thereof. In some embodiments, an exemplary microfluidic device in accordance with the presently-disclosed subject matter is provided that further comprises a cover placed over the microchannel, which is comprised of polydimethylsiloxane.

Still further provided, in some embodiments of the presently-disclosed subject matter, are methods of electrokinetically separating one or more molecules in a sample. In some embodiments, a method is provided that comprises: providing a microfluidic device in accordance with the presently-disclosed subject matter; placing a sample in the input reservoir; and, generating an electric field through the microchannel to induce molecules from the sample in the input reservoir to migrate into the microchannel and up to or through the carbon nanotube membranes to thereby produce electrokinetic separation of the molecules from the sample. In some embodiments of the presently-disclosed methods, the molecules are proteins, DNA, or RNA. In some embodiments, the molecule is a protein that has a molecular weight that is greater than 17 kDa. In some embodiments, the molecules are labeled with a fluorescent probe.

With regard to the electrokinetic separation of the molecules, in some embodiments of the presently-disclosed methods, the electrokinetic separation comprises electrophoretic separation, electroosomotic separation, or both. In some embodiments, the electric field that is generated is achieved by applying a potential of about 10 V to about 50 V.

Advantages of the presently-disclosed subject matter will become evident to those of ordinary skill in the art after a study of the description, Figures, and non-limiting Examples in this document.

BRIEF DESCRIPTION OF THE DRAWINGS

FIGS. 2(a)-2(k) include various diagrams depicting the fabrication sequence of an exemplary microfluidic device in accordance with the presently-disclosed subject matter, including: (a) provision of a blank quartz substrate; (b) sputtering of a triple layer of Cr, Au, and Cr; (c) spinning on a photoresist (PR) layer; (d) photolithography by exposure to ultraviolet (UV) light followed by development; (e) Cr/Au/Cr etching to expose the quartz; (f) quartz etching in BOE 6:1; (g) ultrasonication to remove any overhang; (h) iron (Fe) deposition by e-beam evaporation; (i) lift-off of Fe using acetone, followed by Cr/Au/Cr etching; (j) chemical vapor deposition growth of carbon nanotubes inside microchannels; and, (k) bonding of a polydimethylsiloxane (PDMS) cover to create a closed microchannel.

FIG. 5A is a graph depicting the thickness of various strips of carbon nanotube membranes where the carbon nanotube membrane thickness in micrometers (y-axis) is plotted against the strip location along the microchannel (x-axis). FIGS. 5B and 5C includes images of SEM micrographs at 5° (FIG. 5B) and 30° (FIG. 5C) angles and showing the thickness of a carbon nanotube membrane strip.

FIG. 15A includes images showing the electrokinetic flow of Protein A (*) and Neutravidin (****) through an exemplary microfluidic device at various time intervals. FIG. 15B and FIG. 15C are graphs depicting pixel intensity data measured from fluorescence of the proteins where pixel intensity (A.U., y-axis) is measured at various distances (μm, x-axis) along the length of the microchannel at 30 s (FIG. 15B) and at 75 s (FIG. 15C).

FIG. 16A includes images showing the electrokinetic flow of Protein A, Neutravidin, and Phosphorylase B through an exemplary microfluidic device at various time intervals. FIG. 16B and FIG. 16C are graphs depicting pixel intensity data measured from fluorescence of the proteins where pixel intensity (A.U., y-axis) is measured at various distances (μm, x-axis) along the length of the microchannel at 75 s (FIG. 16B) and at 130 s (FIG. 16C).

DESCRIPTION OF EXEMPLARY EMBODIMENTS

Figure 1A:
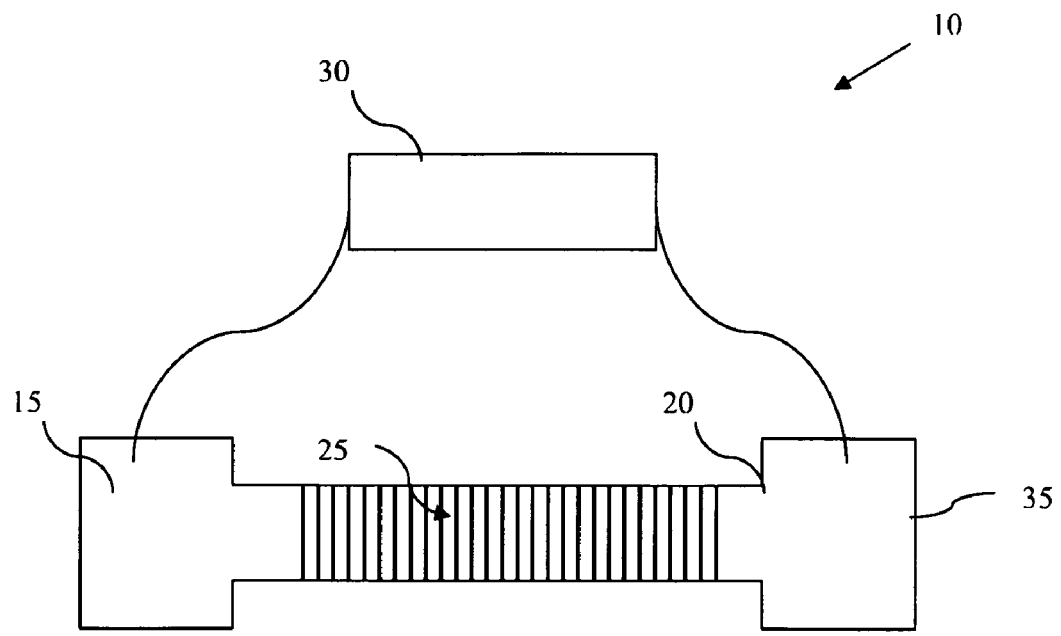
FIG. 1A is a perspective view of an exemplary microfluidic device in accordance with the presently-disclosed subject matter, which includes a plurality of carbon nanotube membranes arranged in strips that are spaced at uniform predetermined intervals along the length of the microchannel.

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

While the following terms are believed to be well understood by one of ordinary skill in the art, definitions are set forth to facilitate explanation of the presently-disclosed subject matter.

Unless defined otherwise, all technical and scientific terms used herein have the same meaning as commonly understood by one of ordinary skill in the art to which the presently-disclosed subject matter belongs. Although any methods, devices, and materials similar or equivalent to those described herein can be used in the practice or testing of the presently-disclosed subject matter, representative methods, devices, and materials are now described.

Following long-standing patent law convention, the terms "a," "an," and "the" refer to "one or more" when used in this application, including the claims. Thus, for example, reference to "a protein" includes a plurality of such proteins, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods.

In order to provide high impedance to macromolecular flow and thereby increase separation efficiency, it is desirable to have submicron-sized pores and an interweaving pattern of carbon nanotube (CNT) strands as opposed to rigid posts. Since CNT meshes can be created with submicron-sized spacing, they are capable of serving as a sieving matrix in a protein electrophoresis separation device. To that end, the presently-disclosed subject matter provides new micro fluidic devices and methods of using the same for the electrokinetic separation of one or more molecules in a sample.

Figure 1B:
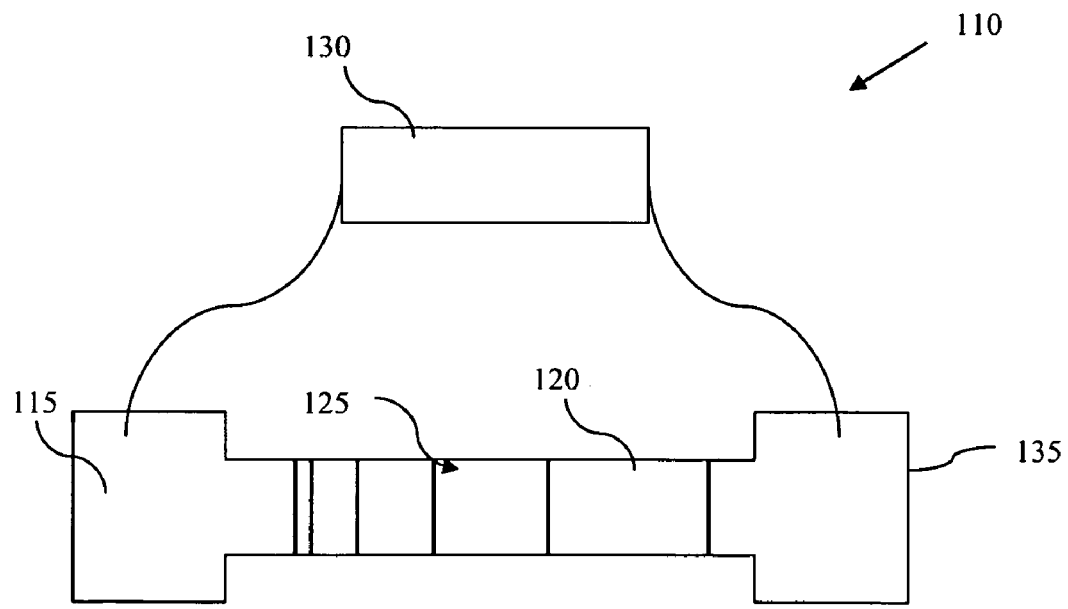
FIG. 1B is a perspective view of another exemplary microfluidic device in accordance with the presently-disclosed subject matter, which includes a plurality of carbon nanotube membranes that are spaced at predetermined intervals that vary along the length of the microchannel.

Referring first to FIGS. 1A and 1B, in some embodiments of the presently-disclosed subject matter, a microfluidic device 10,110 is provided that comprises: an input reservoir 15,115 for receiving a sample containing one or more molecules of interest; a microchannel 20,120 in fluid communication with the input reservoir 15,115; two or more carbon nanotube membranes 25,125 disposed at predetermined intervals within the microchannel 20,120; and a means 30,130 for generating an electric field through the microchannel 20,120 such that the electric field induces molecules from the sample in the input reservoir 15,115 to migrate into the microchannel 20,120 and through the two or more carbon nanotube membranes 25,125 to thereby produce electrokinetic separation of molecules from the sample. Furthermore, as shown in the exemplary embodiments depicted in FIGS. 1A and 1B, an exemplary microfluidic device can also include an exit reservoir 35,135 positioned at the distal end of the microchannel 20,120 for collecting one or more molecules of interest subsequent to their migration through the microchannel 20,120.

Figure 18:
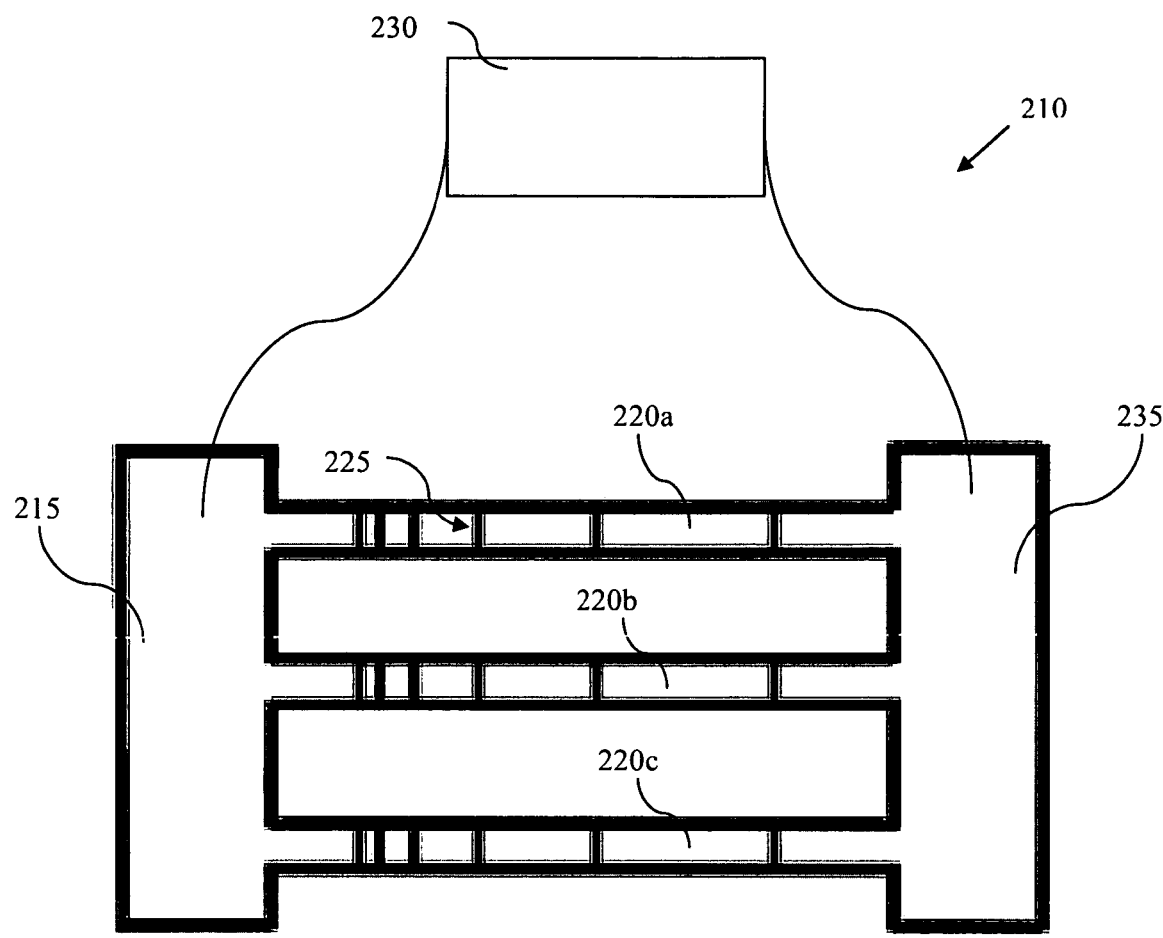
FIG. 18 is a perspective view of another exemplary microfluidic device in accordance with the presently-disclosed subject matter, which includes a plurality of microchannels that are each in fluid communication with an input reservoir, and which also includes a plurality carbon nanotube membranes that are spaced at predetermined intervals that vary along the length of each microchannel.

Referring now to FIG. 18, in some embodiments f the presently-disclosed subject matter, a microfluidic device 210 is provided that comprises: an input reservoir 215 for receiving a sample containing one or more molecules of interest; a plurality of microchannels 220a, 220b, 220c, where each microchannel 220a, 220b, 220c is in fluid communication with the input reservoir 215; two or more carbon nanotube membranes 225 disposed at predetermined intervals within each microchannel 220a, 220b, 220c; and a means 230 for generating an electric field through each microchannel 220a, 220b, 220c such that the electric field induces molecules from the sample in the input reservoir 215 to migrate into each of the microchannels 220a, 220b, 220c and up to or through the two or more carbon nanotube membranes 225 to thereby produce electrokinetic separation of molecules from the sample. Additionally, as shown in the exemplary embodiment depicted in FIG. 18, an exemplary micro fluidic device comprised of a plurality of microchannels 220a, 220b, 220c can also include an exit reservoir 235 that is in fluid communication with each of the microchannels 220a, 220b, 220c and is positioned at the distal end of each of the microchannels 220a, 220b, 220c for collecting one or more molecules of interest subsequent to their migration through the microchannel 220a, 220b, 220c.

As used herein in reference to the devices of the presently-disclosed subject matter, the term "microfluidic" refers to structures or devices through which one or more fluids are passed or directed, and wherein one or more of the dimensions of the device or structure is less than 1000 micrometers. For example, in some embodiments of the presently-disclosed subject matter, a microfluidic device is provided that comprises a microchannel with a length on the order of several millimeters (e.g. 3.175 mm), but comprises a width on the order of several hundred micrometers (e.g. 500 μm) and a depth also on the order of micrometers (e.g. 1.7 μm).

The term "microchannel" as used herein includes elongated structures wherein the longitudinal dimension exceeds that of the diameter or cross-sectional dimension of the microchannel, but can also be used herein in reference to cavities or tunnels of any desired shape or configuration through which various fluids can be directed. Such a microchannel can, for example, comprise a flow-through channel through which fluid is continually passed or, alternatively, can comprise a channel for holding a specified amount of a particular fluid.

Referring now to FIGS. 2(a)-2(k), the microfluidic devices of the presently-disclosed subject matter can be fabricated by employing photolithography methodologies known to those of ordinary skill in the art and by also utilizing chemical vapor deposition (CVD) in conjunction with a CVD growth catalyst deposited on a suitable substrate. In some embodiments, the input reservoir and/or the microchannel is comprised of quartz, silicon, alumina, glass, plastic, or combinations thereof. In some embodiments, and as shown in FIG. 2(a) and FIG. 2(b), a suitable substrate, such as quartz, is first provided and a masking layer is deposited onto the quartz substrate by sputtering to protect the portions of the substrate that are not to be patterned in subsequent etching procedures. Next, as shown in FIG. 2(c), a photoresist layer is spun onto the outermost masking layer. This step is followed by patterning of the device features using a suitable mask and subsequent exposure to ultraviolet (UV) light and development in positive resist developer, as depicted in FIG. 2(d). Etching is then performed to expose the substrate and to create a suitable microchannel or other desired features (e.g., reservoirs) in the substrate. While a grooved channel configuration is shown in FIGS. 2(e) to 2(g), it is contemplated that the microchannel and its cross-section can be configured to provide other geometries, which may be more desirable for alternative applications.

FIG. 2(h) shows the deposition of a CVD growth catalyst on the substrate. Although an iron layer is depicted in FIG. 2(h), it is also contemplated that colloidal iron particles, iron nanoparticles, iron oxides, iron nitrates, and ferromagnetic materials, such as nickel and cobalt, can also be used as a CVD growth catalyst. In some embodiments, the layer of iron that is deposited on the substrate is a thin film layer having a thickness of about 5 nm, and is deposited using thin film deposition techniques, such as electron beam evaporation, followed by lift-off and metal etching.

Figure 3:
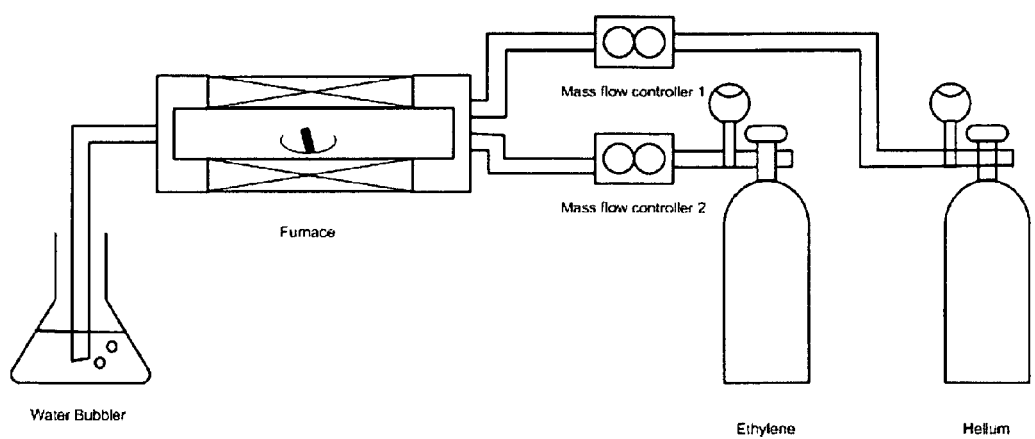
FIG. 3 is schematic diagram depicting an exemplary system employed for the chemical vapor deposition (CVD) growth of carbon nanotubes.

As shown in FIG. 2(j), CNTMs are then grown in the microchannel. With reference to FIG. 3, the CNTMs can be grown by employing an apparatus comprising a high-temperature CVD furnace to effect pyrolysis of a hydrocarbon reaction mixture, with the CNTMs being grown by passing the hydrocarbon reaction mixture over the iron catalyst in the CVD furnace. For example, in some embodiments, the CNTMs can be grown by a thermal CVD process in which ethylene is used as the carbon source and is introduced into the carbon furnace for a predetermined time period (e.g., 1 hour) once the furnace has reached an elevated temperature. As another example, in some embodiments, CNTMs can be grown by a thermal CVD process in which ethylene is used as the carbon source and a hydrogen/argon mixture is used as a carrier gas at elevated temperatures (e.g., 700° C.) for a predetermined time period (e.g., 15 minutes) sufficient to grow the CNTMs.

After growing the CNTMs, a cover can then be placed over the microchannel to enclose the CNTMs within the microchannel. In some embodiments of the presently-disclosed microfluidic devices, the cover is comprised of polydimethylsiloxane (PDMS).

Referring now to FIG. 4, in some embodiments of the presently-disclosed subject matter, the CNTMs grown by the above-described process are grown by self-assembly on a surface of the microchannel. For example, in some embodiments, the CNTMs are comprised of CNTs that grow from the surface of the microchannel to form an intertwined freestanding CNTM across a discrete area. In some embodiments, the CNTs are about 15 nanometers to about 135 nanometers in diameter. In some embodiments, the CNTMs include irregularly sized pores defined between the carbon nanotubes.

By varying the thickness of the Fe thin-film that is deposited on the surface of the microchannel, Applicants have discovered that both the parameters of the CNTs and the irregularly sized pores within the CNTM can be modified so as to provide a CNTM with pores that are suitably sized for a particular application. Applicants have discovered that a smaller iron layer (e.g., 2 nm) yields CNTs of smaller diameter (e.g., 15-25 nm) that more readily intertwine during the growth process and more completely occupy the interstitial spaces between the CNTs than larger diameter CNTs (e.g., 100-135 nm) that are produced by depositing a thicker film of the Fe catalyst (e.g., 20 mm) on a substrate. As such, in some embodiments, the CNTMs of the presently-disclosed subject matter includes pores of variable and tunable size that can readily be modified to present a pore size that is suitable for the separation of molecules of a particular size in a desired separation application. In some embodiments, each of the pores is about 50 to about 200 nanometers in diameter.

In some embodiments of the presently-disclosed microfluidic devices, each of the CNTMs are disposed within the microchannel such that each of the CNTMs spans the width of the microchannel. Through the use of CVD to grow the CNTs directly from the surface of a solid support, e.g. the surface of the microchannel, the CNTs comprise free-standing features that extend randomly from the support and grow into a dense intertwined mesh to form a CNTM. CNTMs produced via this process can be grown on lithographically defined microscale areas to conform to the shape of microfabricated structures, such as a microchannel. See, e.g., U.S. Pat. No. 7,290,667, which is incorporated herein by this reference. Moreover, by patterning the deposition of the Fe catalyst on the microfabricated structure using lithography techniques known to those of ordinary skill in the art, multiple CNTMs can be disposed at specific locations within a microfabricated structure to provide a desired arrangement of CNTMs.

As discussed herein above, in some embodiments of the presently-disclosed subject matter, a microfluidic device is provided that is comprised of CNTMs that are disposed at predetermined intervals within the microchannel. In some embodiments, the predetermined interval between each CNTM can be about 50, about 60, about 70, about 80, about 90, about 100, about 110, about 120, about 130, about 140, about 150, about 200, about 250, about 300, about 400, about 450, about 500, about 550, about 600, about 650, about 700, about 750, about 800, about 850, about 900, about 950, about 1000, about 1050, about 1100, about 1150, about 1200, or about 1250 micrometers. In some embodiments, the predetermined interval ranges from about 50 to about 1200 micrometers.

In some embodiments, the predetermined interval is uniform along the length of the microchannel such that the predetermined interval between each CNTM is the same. With reference to FIG. 1A, as one non-limiting example of a microfluidic device wherein the predetermined interval is uniform along the length of the microchannel, in some embodiments of the presently-disclosed subject matter, a microfluidic device 10 is provided that comprises twenty-eight CNTMs with an edge-to-edge spacing between each CNTM of 60 micrometers.

In some embodiments, the predetermined interval varies along the length of the microchannel such that the predetermined interval between each CNTM is different. With reference to FIG. 1B, as one non-limiting example of a microfluidic device wherein the predetermined interval between each CNTM varies, in some embodiments of the presently-disclosed subject matter, a microfluidic device 110 is provided that is comprised of six CNTMs where the first CNTM, which is closest to the input reservoir 115, is spaced 100 micrometers apart from a second CNTM; the second CNTM is spaced 200 micrometers apart from a third CNTM; the third CNTM is spaced 400 micrometers apart from a fourth CNTM; the fourth CNTM is spaced 800 micrometers apart from a fifth CNTM, and the fifth CNTM is spaced 1200 micrometers apart from the sixth and final CNTM.

In some embodiments, and as shown in FIGS. 1A, 1B, and 18, each of the CNTMs is a strip that is positioned transverse to the longitudinal axis of the microchannel. As used herein, the term "strip," when used in reference to a CNTM, refers to a geometrical shape wherein the longitudinal axis of the CNTM that spans the width of the microchannel is longer than the edge-to-edge width of the particular CNTM. In some embodiments, the strip, or the width of the CNTM, is about 20, about 30, about 40, about 50, about 60, about 70, about 80, about 90, about 100, about 110, or about 120 micrometers wide. In some embodiments, the strip is about 40 to about 120 micrometers wide.

Although, various configurations of CNTMs disposed within a microchannel are contemplated by the presently-disclosed subject matter, Applicants have discovered that by utilizing strips of CNTMs that are positioned transverse to the longitudinal axis of the microchannel, a microfluidic device can be provided that is capable of being used as a means to electrokinetically separate one or more molecules of interest from a sample. Without wishing to be bound by any particular theory, it is believed that a microfluidic device comprising a single long CNTM, spanning both the length and width of the microchannel, creates a break in a subsequently applied electric field and thus causes a significant interruption in the voltage gradient that is established during the course of electrokinetic separation. By providing a microfluidic device comprised of multiple strips of CNTMs, however, a microfluidic device is provided in which a voltage gradient can be established that more closely approximates a voltage gradient that is observed in a channel without CNTMs, and thus results in an electrokinetic flow that can be used to effectively separate one or more molecules of interest.

Various means for generating an electric field known to those of ordinary skill in the art can be used in conjunction with the presently-disclosed microfluidic devices and methods of using the same. For example, in some embodiments, and as depicted in FIGS. 1A, 1B, and 18, the means for generating an electric field 30, 130, 230 can comprise a power source into which two electrodes may be attached to provide an anode and a cathode. In some embodiments, the means for generating an electric field comprises a pair of electrodes including a first electrode that is positioned at a first end of the microchannel near the input reservoir, and a second electrode that is positioned at a second end of microchannel.

The electrodes of the presently-disclosed microfluidic devices can be comprised of any electrically conductive material through which an electric current may enter and leave. Such electrodes are known to those of ordinary skill in the art and include, but are not limited to, platinum wires. Typically, an exemplary microfluidic device of the presently-disclosed subject matter comprises at least two electrodes such that an anode can be provided on the first end of the microchannel near the input reservoir and a cathode can be provided on a second end of the microchannel, or vice versa. By positioning oppositely charged electrodes at either end of the microchannel, an electrical gradient can thereby be established along the length of the microchannel to effectuate the electrokinetic separation of one or more molecules of interest in a sample.

A variety of molecules can be electrokinetically separated by using the presently-disclosed microfluidic device, including, but not limited to proteins and nucleic acids. In some embodiments, the one or more molecules that are electrokinetically separated include proteins, DNA, or RNA. In some embodiments, the one or more molecules is a protein that has a molecular weight greater than about 17 kDa. In some embodiments, the CNTMs are modified, or tuned, such that the CNTMs of the presently-disclosed microfluidic devices are capable of separating proteins with molecular weights greater than about 115 Da.

In some embodiments of the presently-disclosed subject matter, a method of electrokinetically separating one or more molecules in a sample is provided. In some embodiments, the method comprises: providing a microfluidic device, including an input reservoir for receiving a sample containing one or more molecules of interest, a microchannel in fluid communication with the input reservoir, and two or more carbon nanotube membranes disposed at predetermined intervals within the microchannel; placing a sample in the input reservoir; and generating an electric field through the microchannel wherein the electric field induces molecules from the sample in the input reservoir to migrate into the microchannel and through the two or more carbon nanotube membranes to thereby produce electrokinetic separation of molecules from the sample.

As used herein the phrase "electrokinetic separation" refers to the separation of one or more molecules in a heterogeneous mixture by causing the migration of molecules in a medium through the application of an electric field, regardless of whether the field exerts its motor action on the molecules directly or indirectly, or by means of a displacement of associated species, or by any combination of direct and indirect action. Thus, the phrase "electrokinetic separation" is used herein to refer to any separation that occurs as a consequence of electric-field assisted migration of molecules through a channel. Typically, the primary mechanisms involved in electrokinetic separation are electroosmosis and electrophoresis and, as such, the phrase "electrokinetic flow" is often used to refer to the sum of electroosmotic flow and electrophoretic flow. In some embodiments of the presently-disclosed methods, the electrokinetic separation comprises electrophoretic separation, electroosmotic separation, or both.

The phrase "electrophoretic separation" is used herein to refer to the separation of electrically-charged substances in a sample by the application of an electrical field, which causes the charged substance to migrate toward either a cathode or an anode depending on its net charge and its frictional interaction with the surrounding medium.

The phrase "electroosmotic separation" is used herein to refer to the separation of a particular substance in a sample due to the bulk movement of the liquid in the sample through a medium following the application of an electric field.

As one non-limiting example of a method of electrokinetically separating one or more molecules of interest in a sample in accordance with the presently-disclosed methods, in some embodiments, a sample containing one or more proteins of interest can be placed in the input reservoir of a microfluidic device. An end of a platinum wire can then be inserted into the input reservoir and an end of a second platinum wire can be inserted into the device at or near the end of the microchannel opposite the input reservoir (e.g. in an exit reservoir), to provide an anode and a cathode, respectively. The other ends of the platinum wires can then be attached to a power source to generate an electric field and subsequently produce an electrokinetic separation of the proteins in the sample. In some embodiments of the presently-disclosed methods, the generation of an electrical field is achieved by applying a potential of about 10 V to about 50 V.

As another non-limiting example of a method of electrokinetically separating one or more molecules of interest in a sample in accordance with the presently-disclosed methods, in some embodiments, a sample containing multiple proteins of varying size can be placed in the input reservoir of a microfluidic device that is comprised of multiple microchannels that are arranged substantially parallel to each other microchannel, and which are each in fluid communication with the input reservoir. In some embodiments, the particular CNTMs that are disposed in a particular microchannel include different pore sizes relative to the CNTMs that are found in the other microchannels of the device. When an electric field is subsequently generated to such a device, parallel processing of differently sized molecules, such as proteins, can thus occur at the same time.

The terms "protein", "polypeptide", and "peptide", are used interchangeably herein, to refer to a polymer of the 20 protein amino acids, or amino acid analogs, regardless of its size or function. Although "protein" is often used in reference to relatively large polypeptides, and "peptide" is often used in reference to small polypeptides, usage of these terms in the art overlaps and varies. Thus, the term "protein" as used herein refers to peptides, polypeptides, and proteins, unless otherwise noted. Exemplary proteins include gene products, naturally occurring proteins, homologs, orthologs, paralogs, fragments and other equivalents, variants, and analogs of the foregoing.

The term "nucleic acid" is used herein to refer to deoxyribonucleotides or ribonucleotides and polymers thereof in either single- or double-stranded form, including DNA and RNA. The term "DNA" is used herein to refer to a molecule comprising at least one deoxyrobonucleotide residue. By "deoxyribonucleotide" is meant a nucleotide lacking a hydroxyl group at the 2' position of a β-D-ribofuranose moiety. The term "RNA" refers to a molecule comprising at least one ribonucleotide residue. By "ribonucleotide" is meant a nucleotide with a hydroxyl group at the 2' position of a β-D-ribofuranose moiety. As such, the terms DNA and RNA encompass double stranded DNA and RNA, single stranded DNA and RNA, DNAs and RNAs with both double stranded and single stranded regions, isolated DNA and RNA such as partially purified, essentially pure, synthetic, and recombinantly produced DNA or RNA, as well as altered or analog DNA and RNA, that differs from naturally occurring DNA or RNA by the addition, deletion, substitution, and/or alteration of one or more nucleotides. Such alterations can include addition of non-nucleotide material.

During electrokinetic separation of one or more molecules of interest in a sample, the movement of the one or more molecule of interest can be detected by attaching a label to the molecules. As used herein, the terms "label" and "labeled" refer to the attachment of a moiety, capable of detection by spectroscopic, radio logic, or other methods, to a particular molecule of interest. Thus, the terms "label" or "labeled" refer to incorporation or attachment, optionally covalently or non-covalently, of a detectable marker into a molecule, such as a polypeptide. Various methods of labeling polypeptides are known in the art and can be used. Examples of labels for polypeptides include, but are not limited to, the following: radioisotopes, fluorescent labels, heavy atoms, or chemiluminescent groups. In some embodiments, labels are attached by spacer arms of various lengths to reduce potential steric hindrance.

In some embodiments, the one or more molecules of interest are labeled with an electrochemical probe. In some embodiments, the one or more molecules of interest are labeled with a fluorescent probe.

Fluorescent probes that can be utilized include, but are not limited to fluorescein isothiocyanate; fluorescein dichlorotriazine and fluorinated analogs of fluorescein; naphthofluorescein carboxylic acid and its succinimidyl ester; dylight 405; rhodamine; carboxyrhodamine 6G; pyridyloxazole derivatives; Cy2, 3, 3.5, 5, 5.5, and 7; phycoerythrin; phycoerythrin-Cy conjugates; fluorescent species of succinimidyl esters, carboxylic acids, isothiocyanates, sulfonyl chlorides, and dansyl chlorides, including propionic acid succinimidyl esters, and pentanoic acid succinimidyl esters; succinimidyl esters of carboxytetramethylrhodamine; rhodamine Red-X succinimidyl ester; Texas Red sulfonyl chloride; Texas Red-X succinimidyl ester; Texas Red-X sodium tetrafluorophenol ester; Red-X; Texas Red dyes; tetramethylrhodamine; lissamine rhodamine B; tetramethylrhodamine; tetramethylrhodamine isothiocyanate; naphthofluoresceins; coumarin derivatives (e.g., hydroxycoumarin, aminocoumarin, and methoxycoumarin); pyrenes; pyridyloxazole derivatives; dapoxyl dyes; Cascade Blue and Yellow dyes; benzofuran isothiocyanates; sodium tetrafluorophenols; 4,4-difluoro-4-bora-3a,4a-diaza-s-indacene; Alexa fluors (e.g., 350, 430, 488, 532, 546, 555, 568, 594, 633, 647, 660, 680, 700, and 750); green fluorescent protein; and yellow fluorescent protein. The peak excitation and emission wavelengths will vary for these compounds and selection of a particular fluorescent probe for a particular application can be made in part based on excitation and/or emission wavelengths.

The presently-disclosed subject matter is further illustrated by the following specific but non-limiting examples. Some of the following examples are prophetic, notwithstanding the numerical values, results and/or data referred to and contained in the examples. Further, the following examples may include compilations of data that are representative of data gathered at various times during the course of development and experimentation related to the presently-disclosed subject matter.

EXAMPLES

Example 1

Fabrication of Microfluidic Device

For fabrication of an exemplary microfluidic device, quartz was chosen as a substrate material because it is capable of withstanding the high temperatures that are observed during chemical vapor deposition (CVD) of carbon nanotubes (CNTs), it is optically clear, and because it bonds readily to polydimethylsiloxane (PDMS). 50 mm×25 mm finely-polished and semiconductor-grade quartz substrates (FIG. 2(a)) were obtained (Chemglass; Vineland, N.J.). The obtained substrate was degreased by sonication in an ultrasonication bath in acetone, followed by methanol and DI water, for 5 minutes each. A masking layer, composed of a triple layer of Cr, Au and Cr (FIG. 2(b)), was then deposited by sputtering (Technics 4604 Sputterer; Alexandria, Va.). The masking layer was used to protect the material outside the microchannel from the Buffered Oxide Etch (BOE) during the forthcoming quartz etching step. To deposit the masking layer, chrome was first deposited to a thickness of 40 nm for 1 minute by radio frequency (RF) sputtering in Argon ambient (pressure=30 mTorr; power=350 Watts), followed by 200 nm diode (DC) sputtering of gold for 1 minute (pressure=45 mTorr; power=120 Watts) and 10 nm of chrome deposition again by RF sputtering for 10 s in the same conditions as mentioned above for the previous chrome deposition step. Positive photoresist, AZ 1518 was subsequently spun-on (Solitec Spinner 5100, Calif.) for 20 s at a spread speed of 2000 rpm and spin speed of 4000 rpm (FIG. 2(c)). Soft bake was then performed for 75 s at a temperature of 115° C. on a hot plate to remove any moisture and improve adhesion of photoresist to the Cr layer. Channel features were patterned onto the substrate using a previously made mask by exposure to UV light for 6.5 s (ABM Mask Aligner; San Jose, Calif.).

The quartz substrate was developed in a positive resist developer, Microposit™ MF™-319 (Rohm and Haas Electronic Materials; Philadelphia, Pa.) for a few seconds before rinsing with water and blow drying with nitrogen (FIG. 2(d)). The substrate was then soft baked again on a hot plate at 115° C. for 75 s. The exposed top Cr layer was etched using Micro Chrome Etchant CEP-200 (Microchrome Tech., Inc., San Jose, Calif.) for 10 s. The underlying Au was etched by exposure to potassium iodide (KI) for 20 s. Subsequently, the bottom Cr layer was etched by a second dip in CEP-200 for 90 s or until the underlying glass was visible (FIG. 2(e)).

The microchannel was formed by etching in BOE 6:1 (J. T. Baker, Phillipsburg, N.J.) for 40 minutes with occasional agitation (BOE etch rate in quartz=100 nm/min) The channels were thoroughly rinsed and washed in flowing DI water and blow dried in nitrogen. The undercutting due to wet etching causes an "overhang" of the masking layers above either sidewalls of the microchannel as shown in FIG. 2(f). This masking layer, used previously to pattern etching areas, would also determine the pattern of the catalytic iron layer if left unremoved, and would thus prevent growth of CNTs on the sidewalls. Therefore, the overhang was removed by ultrasonication for only a few seconds so as not to create potholes in the Cr/Au/Cr layer exposing the quartz underneath (FIG. 2(g)). After ultrasonication, the substrate was then thoroughly inspected using an optical microscope to ensure that no potholes were created during the ultrasonication step. If any potholes were found, photoresist was carefully applied by manual means with a cotton swab over the surface outside the microchannel, in order to prevent Fe from depositing outside the microchannel.

Subsequently, the CNT growth catalyst, Fe was deposited (FIG. 2(h)) to a thickness of 6 nm by evaporation at a base pressure of $5 \times 10^{-7}$ Torr using an E-beam Evaporation System (Axxis series; Kurt J. Lesker Co., Philadelphia, Pa.). Iron was then lifted-off in an acetone bath, exposing the underlying chrome, rinsed in methanol and running DI water, followed by Cr/Au/Cr etching (FIG. 2(i)). Chemical vapor deposition was then used to grow the carbon nanotube membranes inside the microchannels (FIG. 2(j)) and a PDMS cover was bonded to the quartz substrate (FIG. 2(k)) as set forth below.

Figures 4A, 4B, 4C:
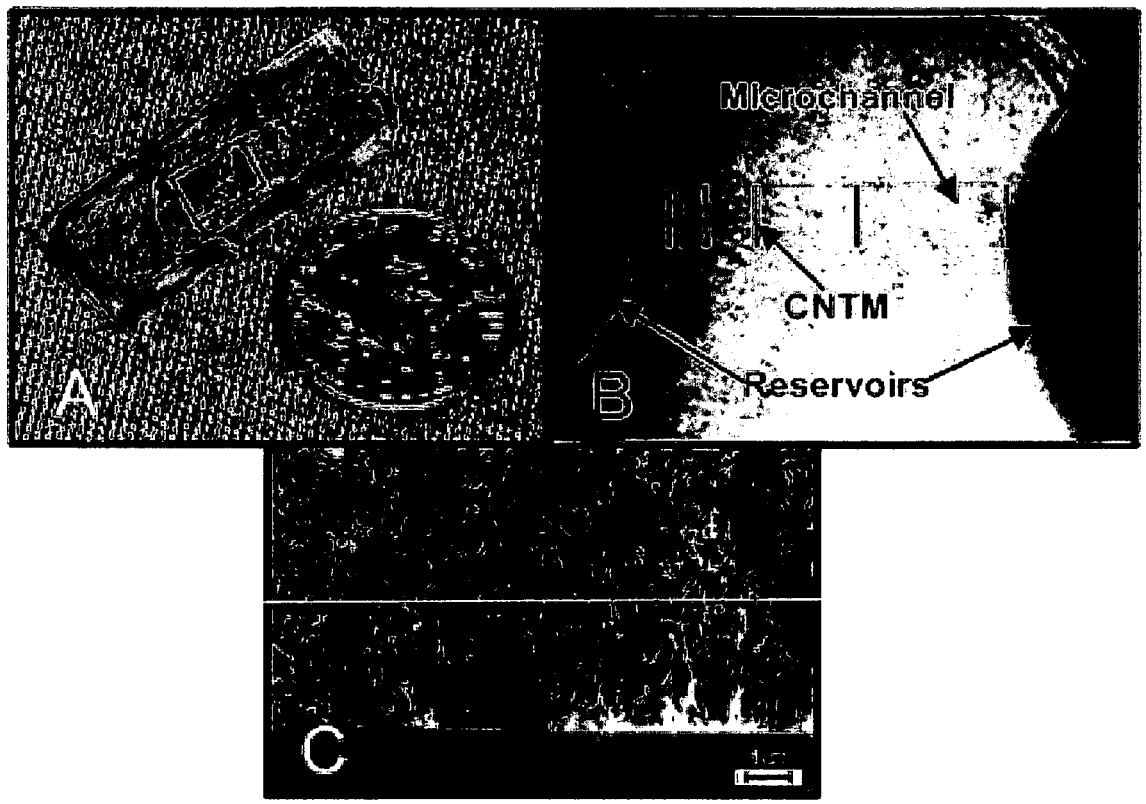
FIGS. 4A-4C includes photographs of an exemplary micro fluidic device in accordance with the presently-disclosed subject matter, including a microscopic image of the microfluidic device relative to a common coin (FIG. 4A), a microscopic image of a portion of the image shown in (FIG. 4A) and showing strips of carbon nanotube membranes disposed within the microchannel (FIG. 4B), and a cross-sectional scanning electron microscope (SEM) image of a carbon nanotube membrane (FIG. 4C).
Figure 6:
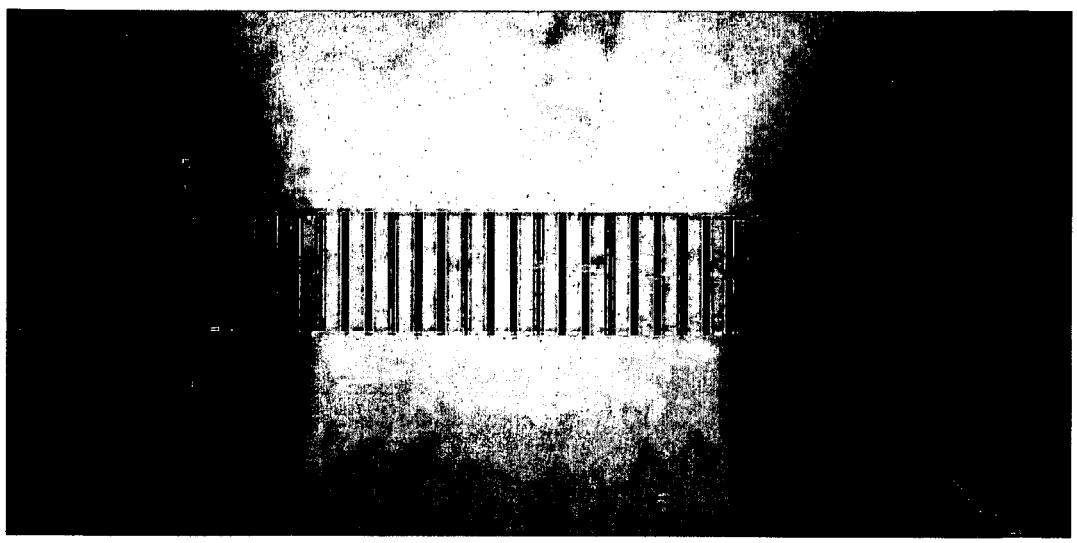
FIG. 6 is a microscopic image of an exemplary microfluidic device, which includes carbon nanotube membranes arranged in strips and spaced at uniform predetermined intervals along the length of the microchannel.

As shown in FIGS. 4A-4C, this process produced a lab-on-a-chip-type microfluidic device that is similar in size to a common coin (FIG. 3A). Further, inspection of the device showed that the process effectively positioned carbon nanotube membranes (CNTMs) at the precise location where the iron was deposited and created strips of CNTMs that spanned the width of the microchannel. A scanning electron microscope image of the CNTMs, including the individual CNTs, is shown in FIG. 4C. Another exemplary microfluidic device produced by the foregoing process, but including approximately 28 CNTM strips, is shown in FIG. 6.

Example 2

Carbon Nanotube Membrane Synthesis

To grow the carbon nanotube membranes via CVD, an apparatus was utilized that included a 4-ft long quartz tube, 2 inches in diameter, that was placed in a CVD furnace between heater coils, with a thermocouple inside the coil housing and a temperature controller. In order to minimize the effects due to contamination, the complete CNT growth set-up, which is shown in FIG. 3, was vacuum-pumped for several hours before every use. The metal tubing and connections leading to the quartz tube were some times heated up with a heat gun, during vacuum pumping, to further enhance out-gassing from the inside of the tubes and connections.

To begin the growth process, the substrate with the evaporated iron-thin film catalyst was calcinated in dry air (100 sccm) by heating in a furnace to 400° C. to remove organic contaminants from the substrate. The temperature was fully ramped up to 400° C. in 10 minutes. Once the temperature was stable, the gas was flowed for 2 minutes at a high flow rate. Subsequently, 10% $H_2$/90% Ar gas (100 sccm) was passed as temperature was increased from 400° C. to 700° C. $H_2$/Ar gas was replaced by ethylene (450 sccm) and flowed for 4 minutes. The furnace was then cooled to room temperature (ramp rate: 20° C./min) while flowing Helium gas at a mass flow rate of 100 sccm. Gas flow was ensured by visual inspection of the water bubbler. Helium served to provide an inert atmosphere at high temperatures inside the furnace.

Example 3

Polydimethylsiloxane Bonding

Polydimethylsiloxane (PDMS) bonding was chosen because of ease of bonding, as well as optical clarity [8], which are desirable for microfluidic applications. PDMS pre-polymer and its cross linker (SYLGARD 184 Silicone Elastomer Kit) were purchased. (Dow Corning; Midland, Mich. The pre-polymer and the cross-linker were thoroughly mixed in the ratio of 10:1 by weight and degassed in a vacuum chamber for 1 hr to remove any air bubbles. The polymer mixture was then poured on to a Petri dish up to a height of 2 mm and baked in an oven at 50° C. for 12 hrs. After complete curing, the PDMS sheet was cut in several pieces to the desired size. When the substrate was ready to be bonded, the bonding surfaces of the PDMS sheet and substrate were exposed to oxygen plasma using March CS 1701 Reactive Ion Etching System (March Plasma Systems, Inc.; Concord, Calif.). An RF power of 100 W for 30 s at a vacuum pressure of 100 mtorr was used. After exposure to oxygen plasma, the bonding surfaces were immediately brought into contact and pressed against each other to remove any trapped air bubbles between them. In order to increase the bond strength, rapid aging of the bonded surfaces was carried out in an oven at 50° C. for 12 hrs.

Example 4

Profilometry of Carbon Nanotube Membranes

Surface profilometry was performed on samples after the CVD process. The growth of CNTs (i.e., the thickness of the membrane grown inside the microchannel) was characterized using a Dektak profilometer (Veeco; Woodbury, N.Y.). Measurements from the profilometer were verified from SEM pictures of cross-sections. The stylus radius was 2.5 μm and ultra-low force (0.3 mg) was applied to ensure that the stylus did not penetrate and damage the film, while traversing the width of the microchannel.

Figures 5A, 5B, 5C:
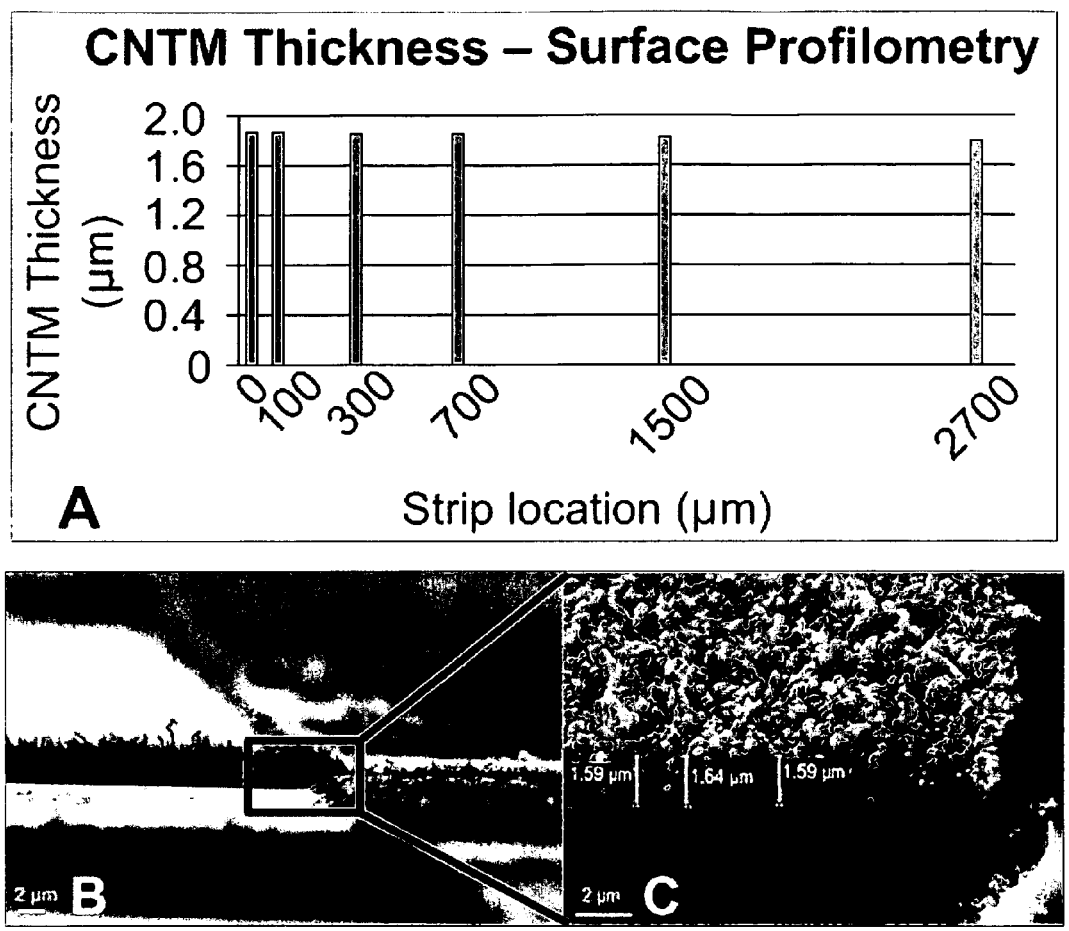
FIGS. 5A-5C include graphs and images depicting the surface profilometry of an exemplary carbon nanotube membrane.

FIG. 5 shows the thickness of individual CNTM strips (FIG. 5B) and a cross-sectional SEM image of the "as-grown" CNTM (FIG. 5C), with an average CNT diameter of approximately 50 nm. Thickness measurements from surface profilometry indicated that the CNTM strips were 1.8-1.9 μm thick (FIG. 5A). SEM images taken at 5° and 30° angles to the surface of the substrate (FIGS. 5B and 5C) validated these values, yielding thicknesses of 1.91 μm and 1.84 μm, respectively.

Example 5

Figures 7A, 7B, 7C:
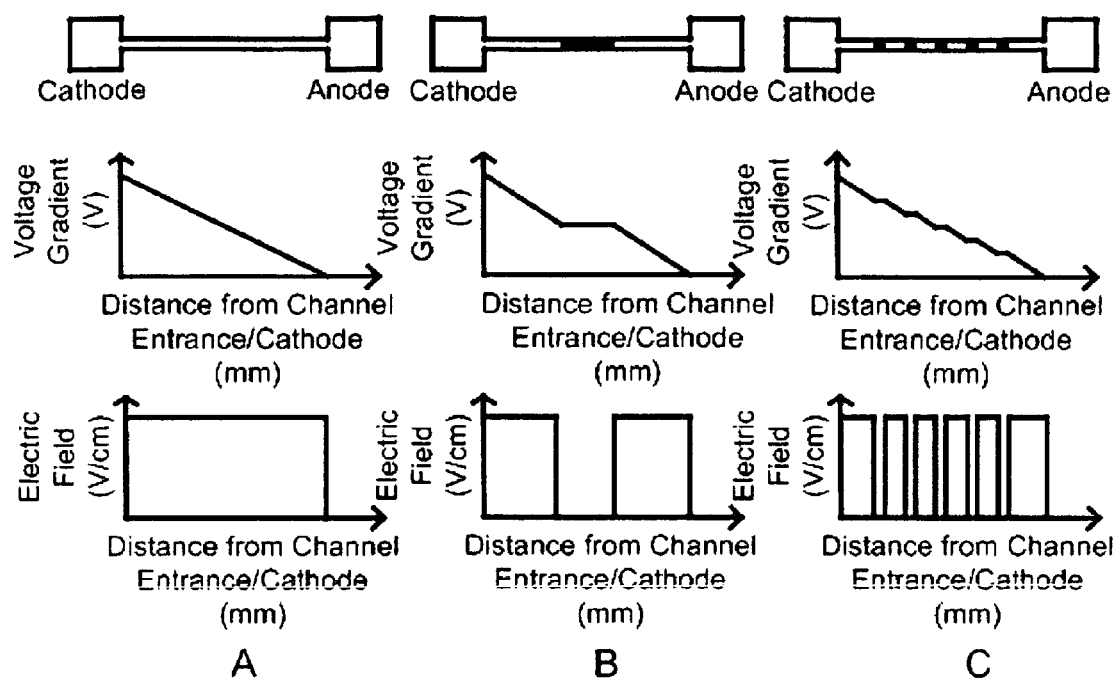
FIGS. 7A-7C show a comparison of voltage gradients between a micro fluidic device with a single long (1000 μm) carbon nanotube membrane (FIG. 7B) and a microfluidic device with multiple narrow (approximately 30 μm) carbon nanotube membranes arranged in strips (FIG. 7C). The voltage gradient depicted in FIG. 7C closely approximates the voltage gradient that is observed in a channel without a carbon nanotube membrane (FIG. 7A), whereas the voltage gradient depicted in FIG. 7B shows a significant interruption in the electric field.

Comparison of Single Carbon Nanotube Membranes with Multiple Carbon Nanotube Membranes To compare the ability of microfluidic devices containing a single CNTM with the ability of microfluidic devices containing multiple CNTMs to electrokinetically separate one or more molecules, a microfluidic device containing a single, 1 mm long CNTM (2 μm thick) located in a microchannel etched in the quartz substrate (500 μm W; 3175 μm L; 1.7 μm D) was first tested with a fluorescein dye (sodium fluorescein, 5 mM in phosphate buffer, 20 mM). Upon the subsequent generation of an electrical field through the microchannel of this first device, flow of the fluorescein dye was observed until the leading edge of the CNTM, where it stopped. There was no migration within the CNTM and beyond it. Without wishing to be bound by any particular theory, it was thought that the absence of electrophoretic migration through the CNTM was due to the conductive nature of the CNTs, which produced a break in the electric field and caused a significant interruption in the voltage gradient (FIG. 7B). The presence of a conductive material thus effectively created two independent electric fields along the length of the channel.

When a microfluidic device comprised of multiple CNTMs (FIG. 6) disposed at predetermined intervals (i.e., strips) was utilized, however, a voltage gradient (FIG. 7C) was established that more closely approximated a voltage gradient in a channel without CNTMs (FIG. 7A). The resulting electroosmotic flow was able to force dye through the narrow CNTMs in this second microfluidic device comprised of CNTM strips. Indeed, although this second device kept the same channel dimensions and cumulative area of the CNTM approximately the same as the previously fabricated single CNTM device, when voltages of 20 V (63 V/cm) and 40 V (126 V/cm) were applied, fluorescein was observed to migrate completely through the channel with an electrokinetic velocity of 0.0056 cm/s and 0.0104 cm/s, respectively.

Example 6

Effects of Iron Film Thickness on Carbon Nanotube Diameter

Figures 8A, 8B, 8C, 8D:
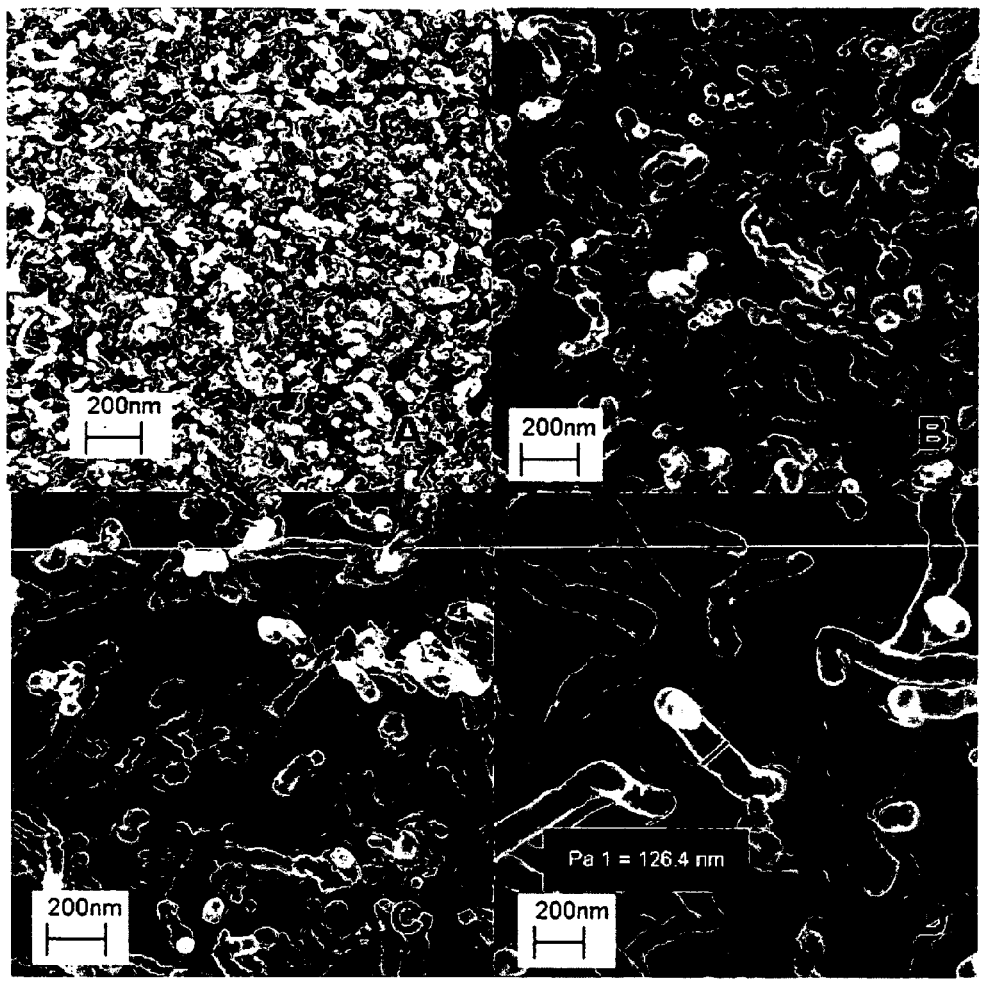
FIGS. 8A-8D includes various SEM images depicting the effect of catalyst film thickness on carbon nanotube diameter and showing that employment of a Fe catalyst film of 2 nm resulted in carbon nanotubes diameters of 15-25 nm (FIG. 8A), that a Fe catalyst film of 5 nm resulted in carbon nanotubes diameters of 45-55 nm (FIG. 8B), that a Fe catalyst film of 10 nm resulted in carbon nanotubes diameters of 45-60 nm (FIG. 8C), and that a Fe catalyst film of 20 nm resulted in carbon nanotubes diameters of 100-135 nm (FIG. 8D).

In order to evaluate the consequence of different Fe film thicknesses and to determine its effect on CNT diameter, CVD was performed on flat quartz substrates without the presence of a channel. SEM images obtained from a total of 4 substrates (one for each thickness) revealed that the diameter of the CNTs increased with increasing thickness of the Fe catalyst film, that is, 2 nm, 5 nm, 10 nm and 20 nm thick iron catalyst films yielded CNTs in the diameter range of 15-25 nm (FIG. 8A), 45-55 nm (FIG. 8B), 45-60 nm (FIG. 8C), 100-135 nm (FIG. 8D), respectively.

It has been proposed that CNT diameter is inversely related to pore size in that an increase in CNT diameter causes the mesh pore size to decrease for a constant mesh volume. This hypothesis was made on the assumption that the density of CNTs (# nanotubes/unit area) will be the same for different diameters, so a larger CNT would take up more volume leaving less intertubular space. However, as shown in FIG. 8, the smaller diameter CNTs intertwined during the growth process and occupied the interstitial volumes/spaces more easily than larger CNTs. Accordingly, these findings indicate that producing CNTs of various diameters can effectively be used to vary the pore size in a particular CNTM. Further, these finding indicate that previous studies indicating that CNT diameter is inversely related to pore size are not entirely accurate, since thinner films of Fe produced CNTMs of higher packing density with smaller pores than those produced by thicker Fe films, as shown in FIG. 8.

Example 7

Comparison of Carbon Nanotube Membranes and Agarose Gels

Figure 9:
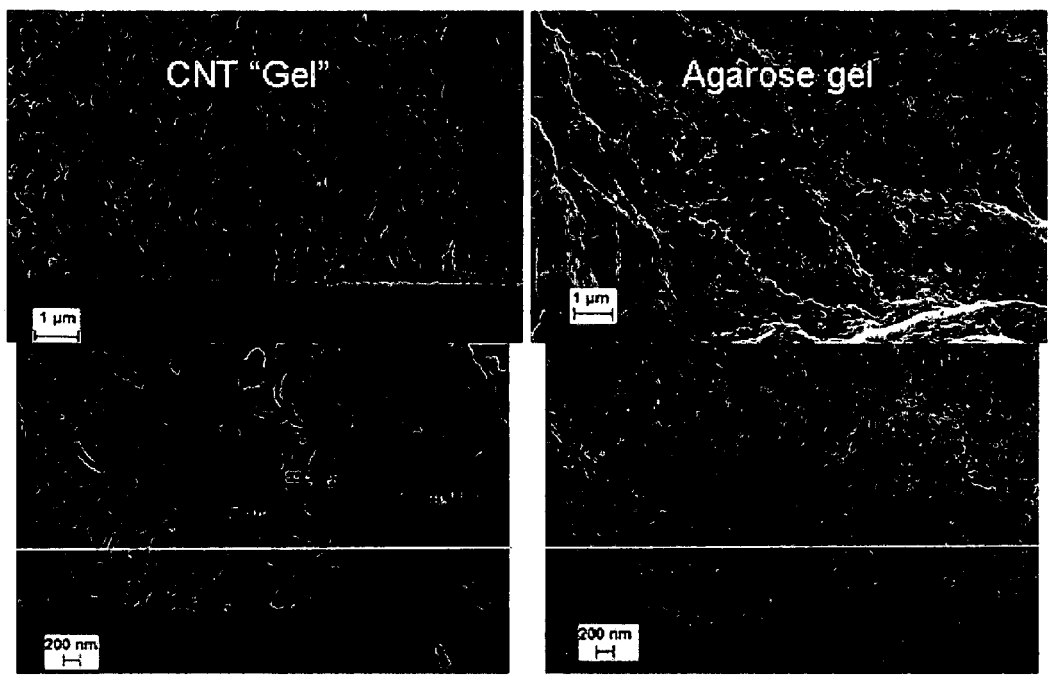
FIG. 9 includes various cross-sectional SEM images showing a comparison of carbon nanotube membranes and agarose gels, which are traditionally used in gel electrophoresis.

Once the CVD process was characterized and evaluated, a comparison between morphologies of a CNTM grown on a 5 nm thick Fe thin film and an agarose gel was performed using electron microscopy. FIG. 9 shows cross-sectional SEM images of a CNTM and an agarose gel at two magnifications. Based on the SEM images, pore size of CNTM was estimated to be 50-200 nm. It was observed that the CNTM had longitudinal pores which were also larger than the pores in the agarose gel. Further, the diameter of the CNT was larger than that of the agarose gel strands. From these SEM images, even though it was possible to use catalyst film thickness of under 5 nm to produce lower pore size to match that of the agarose, a 5 nm Fe film thickness was chosen for the remainder of the experiments because lower thicknesses lead to oxidation of the Fe thin-film, over a few days, necessitating CVD growth immediately after film deposition.

Example 8

Protein Separation Characterization

Fluorescence microscopy was implemented to characterize the CNTM-filled microfluidic devices for their ability to separate proteins. The protein separation characterization set-up consisted of a Keithley 2400 sourcemeter (Keithley Instruments, Inc., Cleveland, Ohio) and an inverted research-grade fluorescence microscope (ECLIPSE TE2000-E, Nikon Instruments, Inc., Melville, N.Y.). Filter blocks were necessary to image a specific fluorescent label, filtering out light emitted by the other fluorescent labels in the FOV. Tables 1 and 2 provide excitation and emission spectra of the filter blocks and fluorophores used to label the proteins. Table 3 provides a list of the proteins used to analyze the ability of the presently-disclosed microfluidic devices to electrokinetically separate proteins.

TABLE 1

| Filter block | Fluorophore | Excitation (nm) | Emission (nm) | Dichroic (nm) |
|---|---|---|---|---|
| Green | Rhodamine | 528-553 (green) | 590-650 (orange/red) | 565 |
| Blue | Fluorescein | 465-495 (blue) | 515-555 (green) | 505 |
| UV | Dylight 405 | 380-395 (purple) | 415-485 (blue) | 405 |

TABLE 2

| Fluorophore | Excitation (nm) | Emission (nm) | MW (g/mol) | Molar extinction coefficient ($M^{-1}cm^{-1}$) |
|---|---|---|---|---|
| Rhodamine | 544 (green) | 576 (red) | 527 | 60,000 |
| Fluorescein | 491 (blue) | 518 (green) | 473 | 70,000 |
| Dylight 405 | 400 (purple) | 420 (light blue) | 793 | 30,000 |

TABLE 3

| Proteins/ Fluorophore | MW (kDa) | Concentration (mM) | Concentration (mg/ml) | Isoelectric Point |
|---|---|---|---|---|
| Aprotinin/ Fluorescein, Bovine, Recombinant, (lyophilized) | 6.5 | 0.3 | 2 | 10.5 [78] |
| Lysozyme/ Fluorescein, Human (lyophilized) | 17 | 0.3 | 5.1 | 10.9 [79] |
| Trypsin Inhibitor/Dylight 405, Soybean (lyophilized) | 20 | 0.3 | 6 | 4.5 [80] |
| Protein A/ Rhodamine, *Staphylococcus aureus* (lyophilized) | 42 | 0.3 | 12.6 | 5.1 [81] |
| Neutravidin/ Fluorescein, Egg white | 66 | 0.3 | 19.8 | 6.3 |
| Plasma Plasminogen/ Dylight 405, Human (lyophilized) | 90 | 0.3 | 27 | 6.4-8.5 [82] |
| Phophorylase B/Dylight 405, rabbit muscle | 97 | 0.3 | 29.1 | 6.5 [83] |

To evaluate the electrokinetic migration of proteins, electrophoresis on Aprotinin (6.5 kDa) and Protein A (42 kDa) were performed separately but under identical testing conditions on two different microfluidic devices. Both devices that were employed in this evaluation had similar microchannel dimensions (width=483.20+/−3.59 μm; depth 1.60+/−0.04 μm; length 3175 mm) and CNTM dimensions (length of the strips=41.83+/−1.11 μm; CNTM thickness 2.84+/−0.48 μm). However, the first device (design type C; depicted in FIG. 1A) was comprised of 28 CNTM strips with an edge-to-edge spacing of 60 μm between the strips, while the second device (design type F; depicted in FIG. 1B) was comprised of 6 CNTM strips with increased edge-to-edge spacing of 100, 200, 400, 800, and 1200 μm between the respective CNTM strips.

Figure 10:
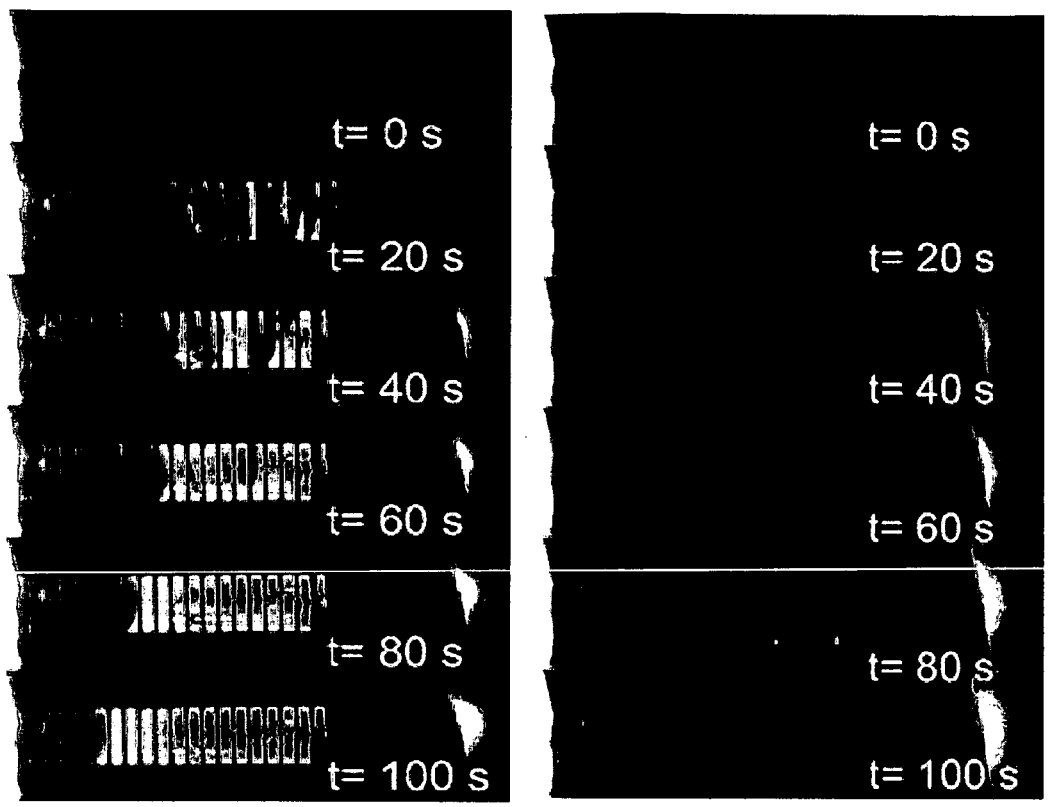
FIG. 10 includes photographs showing the electrokinetic flow of Protein A (left images) and Aprotinin (right images) through an exemplary microfluidic device, including 28 strips of carbon nanotube membranes, over time(s).

On applying a voltage of 30 V between the reservoirs in design type C (FIG. 1A), both proteins migrated the entire length of the microchannel (to the exit reservoir) in approximately 20 s (FIG. 10). In the case of Protein A, accumulation of the protein was observed ahead of 10 (approximately located in the center of the microchannel) out of 28 strips that were spanning the length of the microchannel (FIG. 10, left image). Over time, the accumulation increased in length until the band was so long that it reached the input reservoir. At the same time, the fluorescence observed at the exit reservoir was increasing in size with time, indicating that there was a constant flow of proteins to the exit reservoir.

In the case of Aprotinin, no accumulation was observed ahead of the CNTM strips (FIG. 10, right image). However, accumulation of Aprotinin in the exit reservoir increased with time indicating that there was flow of the protein through the CNTMs even though no accumulation was observed ahead of the strips.

Figure 11:
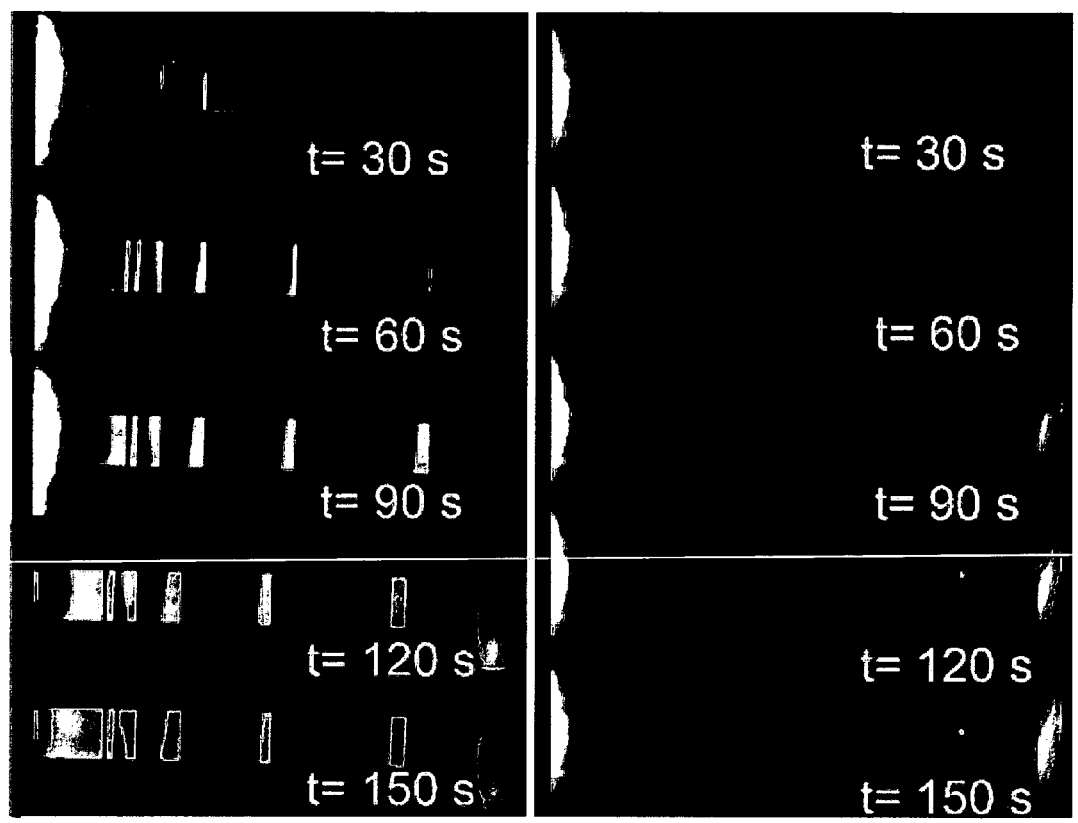
FIG. 11 includes photographs showing the electrokinetic flow of Protein A (left images) and Aprotinin (right images) through an exemplary microfluidic device, including 6 carbon nanotube membrane strips, over time(s).

Similarly, electrophoresis of Protein A and Aprotinin was performed separately on design type F (FIG. 1B) using identical conditions. As shown in FIG. 11, it was again observed that Protein A accumulated ahead of the strips and formed bands, whereas, Aprotinin did not. All the strips produced bands, in the case of Protein A (FIG. 11, left image). Approximately 90 s after the application of the electric field, the Protein A band that formed ahead of the first strip significantly increased in length more than those ahead of the other strips as time progressed (compare t=90 s and t=150 s) and eventually became so long that it almost extended into the input reservoir. A similar observation was also made in the previous experiment in design type C (FIG. 1A). However, bands ahead of the $4^{th}$, $5^{th}$ and $6^{th}$ strips increased in size up to 60 seconds after which they saturated in size, indicating that accumulation ahead of the first two strips reached a critical limit that prevented incoming molecules from migrating further. In the case of Aprotinin (FIG. 11, right image) however, no accumulation was observed indicating that the smaller molecule was able to migrate freely through the pores in the CNTM strips.

Example 9

Protein Molecular Weight Characterization

Figure 12:
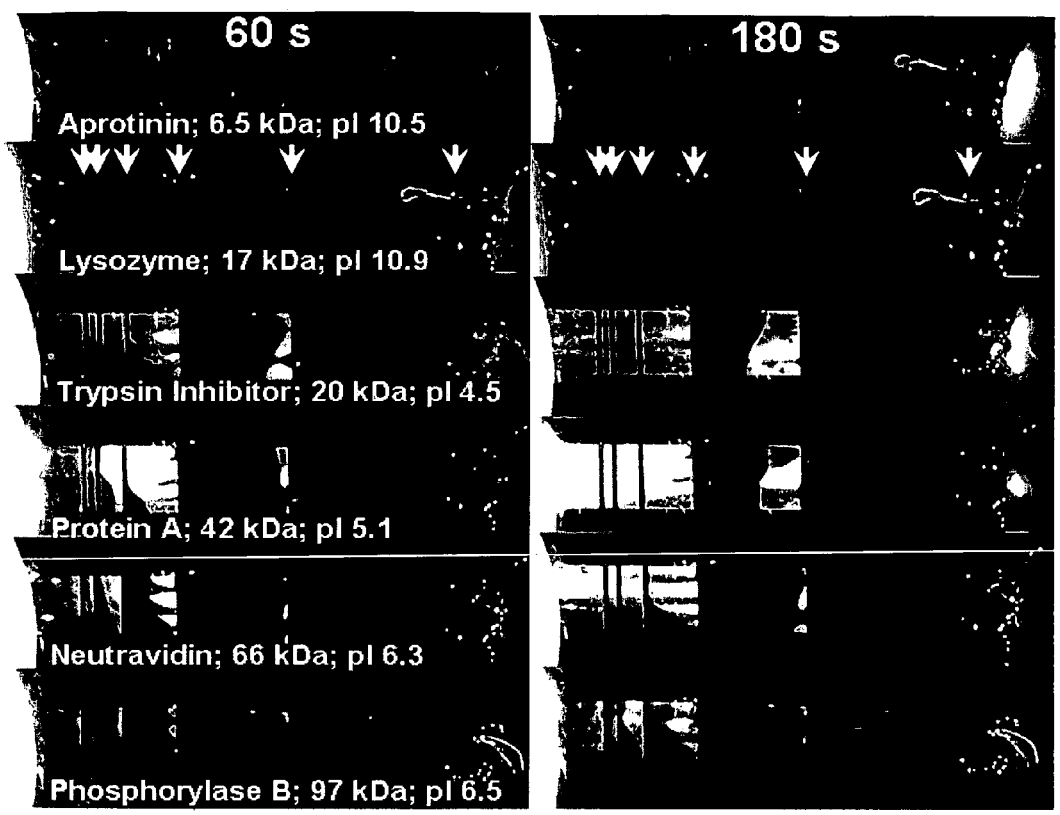
FIG. 12 includes images depicting the electrokinetic flow of proteins of various molecular weights (6.5 kDa to 97 kDa) through an exemplary microfluidic device at 60 s and at 180 s.

Cut-off molecular weight (MW) refers to the MW of a particular protein above which accumulation occurs ahead of the CNTMs and below which proteins freely migrate through the CNTM strips and cause no accumulation. In order to establish the cut-off MW for a CNTM grown from an 5 nm thick Fe thin film, proteins of various molecular weights (6.5-97 kDa) were individually flowed by electrophoresis through the channel using a microfluidic device of design type F (FIG. 1B). The voltage applied was 50 V. It was observed that Aprotinin (6.5 kDa) and Lysozyme (17 kDa) did not form bands, whereas, Soybean Trypsin Inhibitor (20 kDa), Protein A (42 kDa), Neutravidin (66 kDa), Plasminogen (90 kDa; not shown in FIG. 12) and Phosphorylase B (97 kDa) accumulated and formed bands ahead of the CNTM strips (FIG. 12). This observation indicated that a cut-off MW for these particular CNTMs existed and was between 17 and 20 kDa. It was observed that the accumulation increased with time (compare t=60 s and t=180 s). Also, the length of the band was shorter for larger proteins (compare 20 kDa, 42 kDa, 66 kDa and 97 kDa protein bands ahead of the $5^{th}$ strip), indicating that a larger number of smaller proteins ($\geq$20 kDa) were able to migrate through the CNTMs.

Example 10

Electrokinetic Separation of Protein Mixtures

Figure 13:
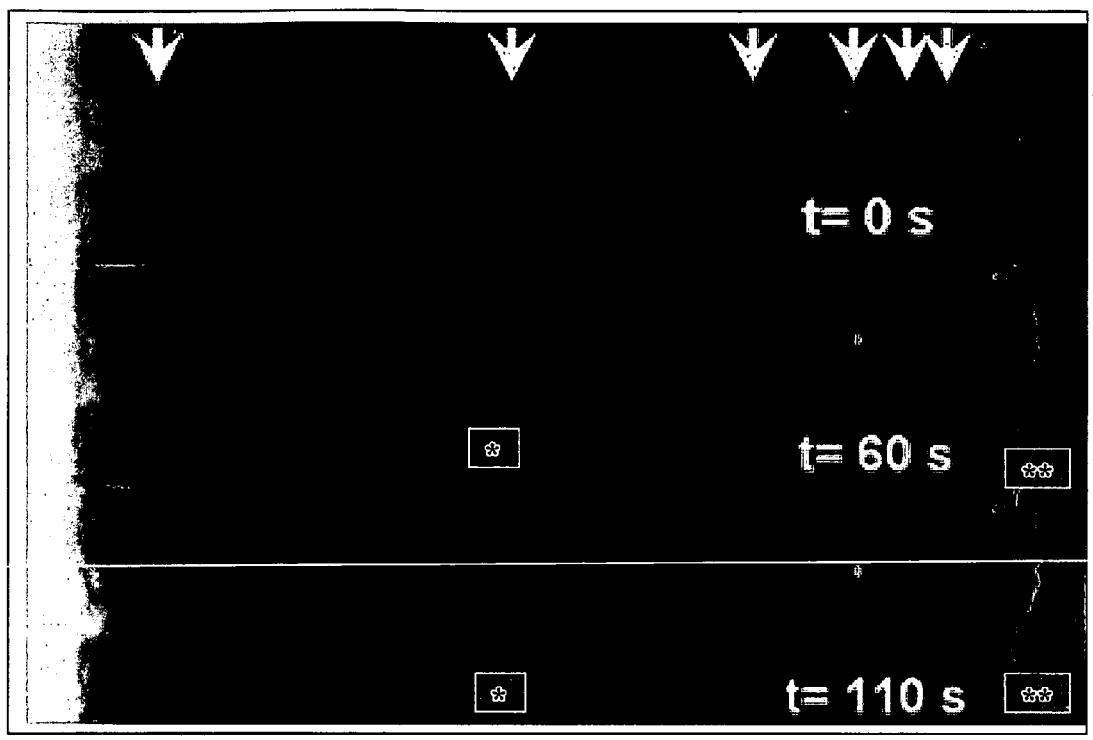
FIG. 13 includes images depicting the electrokinetic flow of a mixture of Protein A (*) and Aprotinin (**) at various time intervals with an applied voltage of 50 V.
Figure 14:
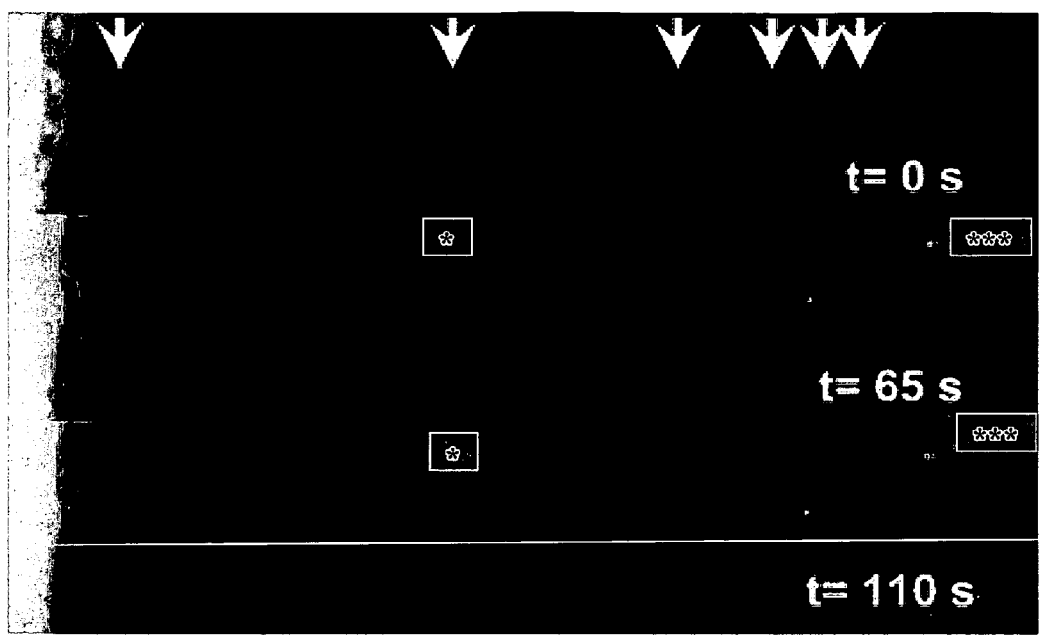
FIG. 14 includes images depicting the electrokinetic flow of Protein A (*) and Lysozyme (***) at various time intervals with an applied voltage of 50 V.

Having established the cut-off molecular weight ($MW_{CO}$) using individual proteins, experiments were conducted to evaluate accumulation when mixtures of proteins were electrokinetically flowed through an exemplary microfluidic device. Two mixtures of 2 proteins were independently electrokinetically flowed through design type F (FIG. 1B) to verify occurrence of the same phenomenon when the proteins are introduced as a mixture. Both mixtures were chosen such that one component was larger than $MW_{CO}$ and the other was smaller. The two mixtures were Aprotinin and Protein A, and Lysozyme and Protein A. On applying a voltage of 50 V, Protein A accumulated ahead of the one of the CNTMs and formed bands that increased in size over time, in both cases of mixtures used. Aprotinin (FIG. 13) and Lysozyme (FIG. 14) flowed freely through all the CNTMs and can be seen to accumulate at the exit reservoir.

Figure 15A:
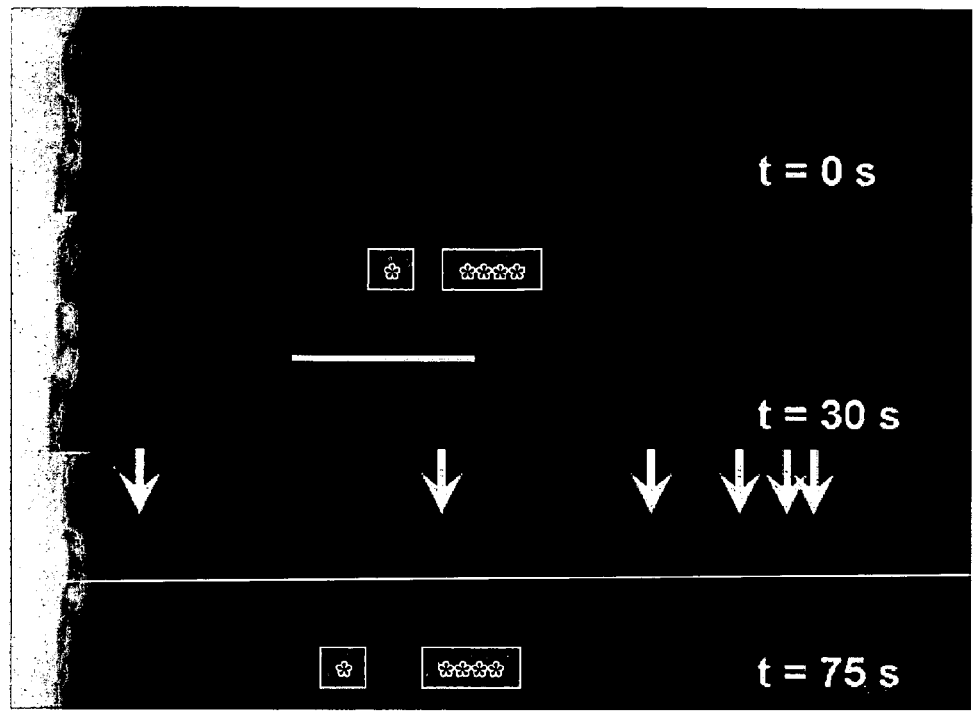
FIGS. 15A-15C include images and graphs depicting the electrokinetic flow of a mixture of Protein A and Neutravidin at various time intervals with an applied voltage of 50 V.
Figure 15B:
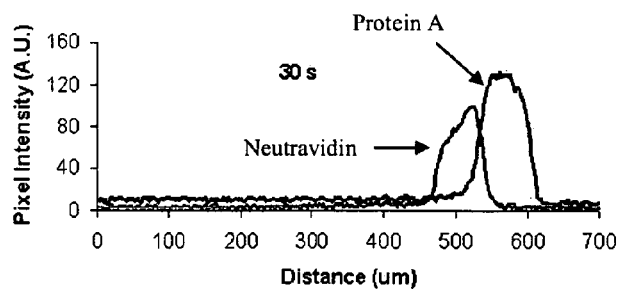
Figure 15C:
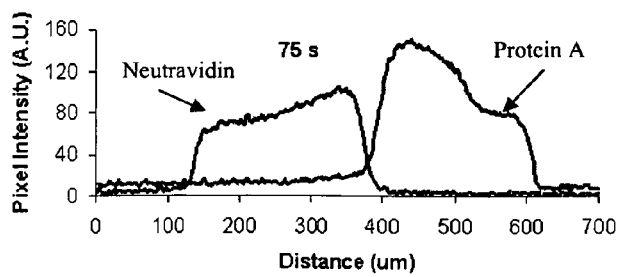

Subsequently, a mixture of 2 proteins, both of which having MWs higher than $MW_{CO}$ was electrokinetically flowed through design type F (FIG. 1B). The proteins used in preparing the mixture were Protein A (42 kDa) and Neutravidin (66 kDa). 50V was applied. Based on previous studies, it was expected that the mixture of the two proteins would accumulate ahead of the CNTMs. However as they accumulated against the CNTM, the two proteins were observed to separate from each other and arrange themselves in increasing order of their molecular weights, i.e., Protein A (42 kDa) band accumulated against the CNTM and Neutravidin (66 kDa) accumulated against the Protein A band (FIG. 15A). Similar to the CNTM that served as a porous mesh in preventing further flow of Protein A and causing accumulation, the Protein A band was acting as a mesh to prevent further flow of Neutravidin. Again, over time both bands increased in size, as shown in FIG. 15A, between time stamps, t=30 s and t=75 s. Protein A, the smaller protein was able to flow through the Neutravidin band, but Neutravidin on account of its larger size was not able to penetrate the Protein A band. FIGS. 15B and 15C shows pixel intensity due to fluorescence at t=30 s and t=75 s, respectively, along a line drawn across the bands. The pixel intensity graph also indicated separation between the proteins. Pixel intensity data verified the occurrence of separation and allowed for quantitative analysis of the proteins, i.e. by quantifying the bands in terms of peak height and band width.

Figure 16A:
FIGS. 16A-16C include images and graphs depicting the electrokinetic flow of a mixture of Protein A, Neutravidin, and Phosphorylase B at various time intervals with an applied voltage of 50V.
Figure 16B:
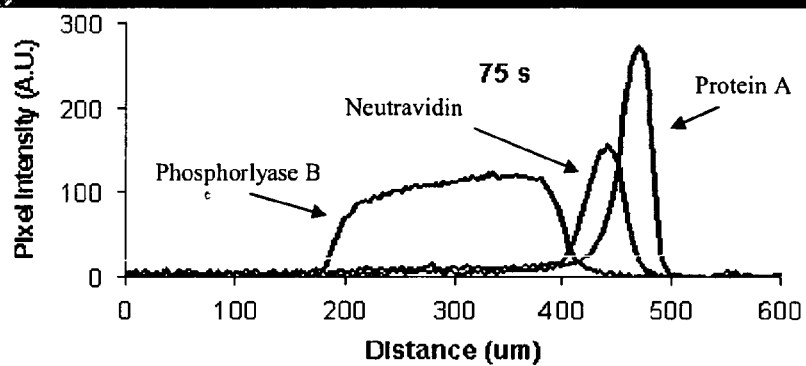
Figure 16C:
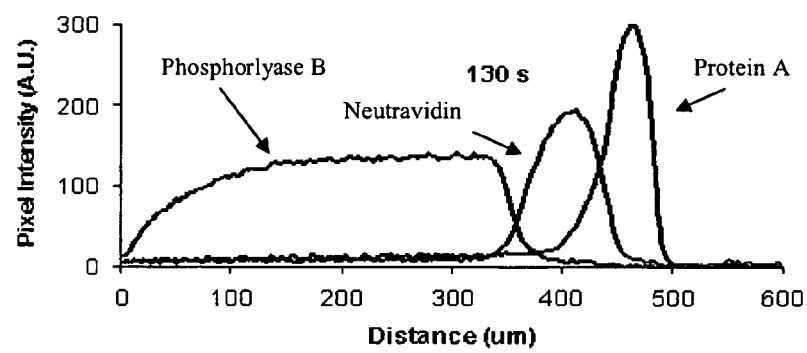

A 3-protein mixture (Protein A, Neutravidin and Phosphorylase B) was then electrokinetically flowed through an alternative microfluidic device design (6 strips, each 60 μm long and spacing was 400 μm in an identical channel; CNTM thickness was identical to those in previous devices) at a smaller voltage of 20 V (FIG. 16A). FIGS. 16B and 16C show band formations at 75 s and 130 s, respectively, and their corresponding pixel intensity data. Pixel intensities at t=0 s was used to remove background noise from the bands produced. The individual protein bands were crisp and the band widths increased with time.

Example 11

Effect of Strip Width

Figures 17A, 17B, 17C, 17D, 17E:
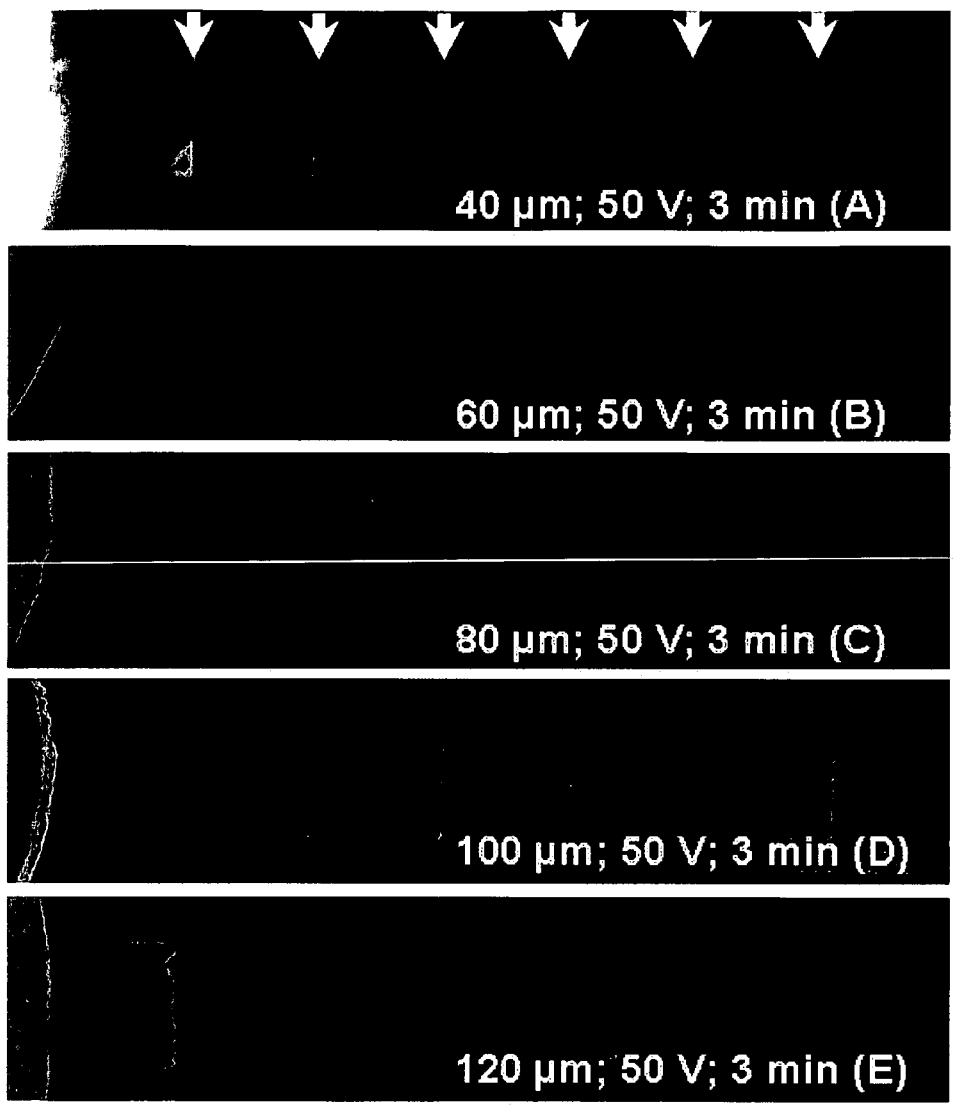
FIGS. 17A-17E includes images depicting the effect of varying the width of carbon nanotube membranes on the electrokinetic flow of proteins in exemplary micro fluidic devices 3 min after the application of a voltage of 50 V to the sample containing the proteins, and including images depicting the effect of carbon nanotube membranes with a width of 40 μm (FIG. 17A), 60 μm (FIG. 17B), 80 μm (FIG. 17C), 100 μm (FIG. 17D), and 120 μm (FIG. 17E).

To evaluate the dependence of accumulation on strip width, microfluidic devices were fabricated that comprised CNTM strips of various widths including a micro fluidic device that included strips widths of 40 µm (FIG. 17A), 60 µm (FIG. 17B), 80 µm (FIG. 17C), 100 µm (FIG. 17D), and 120 µm (FIG. 17E). These microfluidic devices were tested using a 3-protein mixture (Protein A, Neutravidin, and Phosphorylase B) and a voltage of 50 V was applied to evaluate the dependence of accumulation on strip width. FIGS. 17A-E show the results from the devices. Accumulations of proteins ahead of the 120 µm wide CNTM were observed only ahead of the first strip (FIG. 17E). The proteins did not migrate any further into the channel indicating that the 120 µm wide was too long for the proteins to migrate through. Devices made of 100 µm wide CNTM exhibited migration through the strips but did not show separation between the proteins. 80 µm wide CNTMs allowed the proteins to migrate further than the 100 µm wide CNTMs, exhibiting accumulations ahead of the second and third CNTMs. However, no accumulation was observed ahead of the first strip. 60 µm wide CNTMs produced maximum migration of the proteins and bands at all of the CNTMs. The proteins separated and arranged themselves based on their molecular weights and in the process, allowed the smallest protein, namely, Protein A to migrate farthest. However, this observation of increasing length of migration for decreasing CNTM strip widths was not corroborated by 40 µm, which produced protein accumulations only against the $2^{nd}$ strip and no further flow/accumulations were observed. Experiments performed on 120 µm, 80 µm and 60 µm wide CNTM strips indicate a possible dependence of migration and subsequent accumulation on strip width, i.e., narrower CNTMs allow longer migration into the channel.

Example 12

Electrokinetic Separation of Nucleic Acids

To evaluate the ability of the presently-disclosed microfluidic devices to separate nucleic acids (e.g. DNA and RNA), nucleic acids of approximately the same size as the proteins used in the above-described studies are separated using CNTMs with pore sizes identical to those mentioned above. These smaller pore-sized CNTMs cause a smaller "cut-off" MW of proteins/nucleic acids and vice versa, while nucleic acids of other sizes require CNTMs of a different pore size. When mixtures of nucleic acids are analyzed, the arrangement of the nucleic acid bands assumes the same order as what was observed when protein mixtures were separated. The smallest nucleic acid is in the mixture, which is above the "cut-off" molecular weight, accumulates immediately against the CNTM and the largest nucleic acid accumulates farthest from the CNTM, thus indicating that the presently-disclosed micro fluidic devices can effectively be used to separate one or more nucleic acid molecules from a sample.

Throughout this document, various references are mentioned. All such references are incorporated herein by reference, including the references set forth in the following list:

REFERENCES

1. B. Kozulic, Anal. Biochem., 231, 1-12 (1995).
2. A. M. Ahern and R. L. Garrell, Langmuir, 1988, 4, 1162-1168.
3. H. A. Abramson, L. S. Moyer, and M. H. Gorin, "Electrophoresis of Proteins and the Chemistry of Cell Surfaces," New York: Hafner Publishing Co., Inc., 1964.
4. C. D. Furlong and D. J. Beebe, 18th Annual International Conference of the IEEE Engineering in Medicine and Biology Society, Amsterdam, 1996.
5. J. Baselga, M. A. Llorente, I. Hernandez-Fuentes, I. F. Pierola, Eur. Polym. J., Vol. 25, No. 5, 471-475 (1989).
6. Anne-Marie Hecht, Robert Duplessix and Erik Geissler, Macromolecules 1985, 18, 2167-2173.
7. O. Bakajin, N. Ben-barak, J. Peng, A. Noy, 7th International Conference on Miniaturized Chemical and Biochemical Analysts Systems, October 5-9, 2003, Squaw Valley, Calif. USA.
8. B-H. Jo, L. M. Van Lerberghe, K. M. Motsegood and D. J. Beebe, J. Microelectromechanical sys., Vol. 9, No., 1. March 2000.
9. H. Nakanishi, T. Nishimoto, M. Kanai, T. Saitoh, R. Nakamura, T. Yoshida, S. Shoji, Sensors and Actuators 83 2000 136-141.
10. A. Iles, A. Oki, N. Pamme, Proceedings of 2006 International Conference on Microtechnology in Medicine and Biology, Okinawa, Japan, May 2006.
11. U.S. Pat. No. 6,685,810 to Noca, et al., issued Feb. 3, 2004, and entitled "Development of a Gel-Free Molecular Sieve Based on Self-Assembled Nano-Arrays."
12. U.S. Pat. No. 6,773,567 to Wolk, issued Aug. 10, 2004, and entitled "High-Throughput Analytical Systems and Methods of Making Same."
13. U.S. Pat. No. 6,919,046 to O'Connor, et al., issued Jul. 19, 2005, and entitled "Microfluidic Analytical Devices and Methods."
14. U.S. Pat. No. 7,290,667 to Bakajin, et al., issued Nov. 6, 2007, and entitled "Microfluidic Sieve Using Intertwined, Free Standing Carbon Nanotube Mesh as Active Medium."

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A micro fluidic device, comprising:
an input reservoir for receiving a sample containing one or more molecules of interest;
a microchannel in fluid communication with the input reservoir;
two or more carbon nanotube membranes disposed at predetermined intervals within the microchannel, each carbon nanotube membrane having a width along the longitudinal axis of the microchannel that allows for a substantially uninterrupted voltage gradient to be established upon generation of an electric field; and
a means for generating the electric field through the microchannel such that the electric field induces molecules from the sample in the input reservoir to migrate into the microchannel and up to or through the two or more carbon nanotube membranes, thereby producing electrokinetic separation of molecules from the sample.

2. The microfluidic device of claim 1, wherein the carbon nanotube membrane is comprised of carbon nanotubes.

3. The microfluidic device of claim 2, wherein each of the carbon nanotubes are about 15 nanometers to about 135 nanometers in diameter.

4. The microfluidic device of claim 2, wherein each of the carbon nanotube membranes includes irregularly sized pores defined between the carbon nanotubes.

5. The microfluidic device of claim 4, wherein each of the pores is about 50 nanometers to about 200 nanometers in diameter.

6. The microfluidic device of claim 1, wherein each of the carbon nanotube membranes is a strip positioned transverse to the longitudinal axis of the microchannel.

7. The microfluidic device of claim 6, wherein the microchannel has a width, and wherein each of the carbon nanotube membranes spans the width of the microchannel.

8. The microfluidic device of claim 6, wherein the strip is about 40 micrometers to about 120 micrometers wide.

9. The microfluidic device of claim 1, wherein the predetermined interval ranges from about 50 micrometers to about 1200 micrometers.

10. The microfluidic device of claim 1, wherein the predetermined interval is uniform along a length of the microchannel.

11. The microfluidic device of claim 1, wherein the means for generating the electric field comprises a pair of electrodes, a first electrode positioned at a first end of the microchannel near the input reservoir, and a second electrode positioned at a second end of the microchannel.

12. The microfluidic device of claim 1, wherein the input reservoir is comprised of a material selected from the group consisting of quartz, silicon, alumina, glass, plastic, and combinations thereof.

13. The microfluidic device of claim 1, wherein the microchannel is comprised of a material selected from the group consisting of quartz, silicon, alumina, glass, plastic, and combinations thereof.

14. The microfluidic device of claim 1, further comprising a cover placed over the microchannel, wherein the cover is comprised of polydimethylsiloxane.

15. The microfluidic device of claim 1, wherein the carbon nanotube membrane is grown by self-assembly on a surface of the microchannel.

16. A method of electrokinetically separating one or more molecules in a sample, comprising:
   providing a micro fluidic device, including
      an input reservoir for receiving a sample containing one or more molecules of interest,
      a microchannel in fluid communication with the input reservoir, and
      two or more carbon nanotube membranes disposed at predetermined intervals within the microchannel, each carbon nanotube membrane having a width along the longitudinal axis of the microchannel that allows for a substantially uninterrupted voltage gradient to be established upon generation of an electric field;
   placing a sample in the input reservoir; and
   generating the electric field through the microchannel, wherein the electric field induces molecules from the sample in the input reservoir to migrate into the microchannel and up to or through the two or more carbon nanotube membranes, thereby producing electrokinetic separation of molecules from the sample.

17. The method of claim 16, wherein the one or more molecules are selected from the group consisting of proteins, DNA, and RNA.

18. The method of claim 16, wherein the molecules are labeled with a fluorescent probe.

19. The method of claim 16, wherein the electrokinetic separation comprises electrophoretic separation, electroosmotic separation, or both.

20. The method of claim 16, wherein the step of generating the electric field is achieved through applying a potential of about 10 V to about 50 V.

21. The method of claim 16, wherein the one or more molecules is a protein, and wherein the protein has a molecular weight greater than about 17 kDa.

22. A micro fluidic device, comprising:
   an input reservoir for receiving a sample containing one or more molecules of interest;
   a plurality of microchannels, wherein each microchannel is in fluid communication with the input reservoir;
   two or more carbon nanotube membranes disposed at predetermined intervals within each microchannel, each carbon nanotube membrane having a width along the longitudinal axis of the microchannel that allows for a substantially uninterrupted voltage gradient to be established upon generation of an electric field; and
   a means for generating the electric field through each microchannel such that the electric field induces molecules from the sample in the input reservoir to migrate into each of the microchannels and up to or through the two or more carbon nanotube membranes, thereby producing electrokinetic separation of molecules from the sample.

23. The microfluidic device of claim 22, wherein each microchannel is substantially parallel to each other microchannel.

* * * * *